(12) United States Patent
Ueda

(10) Patent No.: US 9,018,335 B2
(45) Date of Patent: Apr. 28, 2015

(54) SUBSTANCES FOR USE AS BISPHENOL A SUBSTITUTES

(75) Inventor: Masahiro Ueda, Kyoto (JP)

(73) Assignee: Empire Technology Development LLC, Wilmington, DE (US)

(*) Notice: Subject to any disclaimer, the term of this patent is extended or adjusted under 35 U.S.C. 154(b) by 208 days.

(21) Appl. No.: 13/139,709

(22) PCT Filed: Dec. 29, 2010

(86) PCT No.: PCT/US2010/062333
§ 371 (c)(1),
(2), (4) Date: Jun. 14, 2011

(87) PCT Pub. No.: WO2012/091701
PCT Pub. Date: Jul. 5, 2012

(65) Prior Publication Data
US 2012/0172568 A1    Jul. 5, 2012

(51) Int. Cl.
C08G 59/06    (2006.01)
C08G 59/24    (2006.01)
C08L 63/00    (2006.01)
C07D 303/28   (2006.01)
C08G 64/06    (2006.01)
C07C 39/16    (2006.01)
C07D 307/44   (2006.01)
C07D 407/14   (2006.01)

(52) U.S. Cl.
CPC ............ C08G 64/06 (2013.01); C07C 39/16 (2013.01); C07D 303/28 (2013.01); C07D 307/44 (2013.01); C07D 407/14 (2013.01); C08G 59/06 (2013.01)

(58) Field of Classification Search
CPC ...... C08L 63/00; C08G 59/06; C07D 407/14; C07D 307/44; C07D 303/28; C07C 39/16
USPC .................... 528/87, 196, 372, 406
See application file for complete search history.

(56) References Cited

U.S. PATENT DOCUMENTS 3,950,451 A  *  4/1976  Suzuki et al. ............... 525/490
4,105,622 A  *  8/1978  Izutu et al. .................. 523/307
4,164,487 A  *  8/1979  Martin ......................... 523/403
4,340,716 A  *  7/1982  Hata et al. ................... 528/100
4,831,110 A     5/1989  Kanno et al.

(Continued)

FOREIGN PATENT DOCUMENTS

EP    1253176 A2  * 10/2002
EP    1548043 A   *  6/2005

(Continued)

OTHER PUBLICATIONS

Robert W. Martin, "The Chemistry of Phenolic Resins," 1956, published by John Wiley & Sons, Inc., pp. 66, 67 and 72-79.*

(Continued)

Primary Examiner — Randy Gulakowski
Assistant Examiner — Ha Nguyen
(74) Attorney, Agent, or Firm — Maschoff Brennan

(57) ABSTRACT

Bis-Phenol A (BPA) can now be replaced in industrial processes by BPA substitutes. The BPA substitutes can have structures that are derivatives of BPA. The BPA substitutes can be used in preparing epoxy composition, polycarbonate compositions, and polysulfonate compositions or for other uses in place of BPA.

13 Claims, 1 Drawing Sheet

(56) References Cited

U.S. PATENT DOCUMENTS

| | | | |
|---|---|---|---|
| 5,002,362 A | | 3/1991 | Kanno et al. |
| 5,147,905 A | * | 9/1992 | Dubois et al. ............... 523/404 |
| 6,277,944 B1 | | 8/2001 | Neumann |

FOREIGN PATENT DOCUMENTS

| | | | |
|---|---|---|---|
| JP | 02-120314 | * | 5/1990 |
| JP | 09-255764 A | * | 9/1997 |
| JP | 09291085 A | * | 11/1997 |

OTHER PUBLICATIONS

Lee et al., "Handbook of Epoxy Resins," 1967, published by McGraw-Hill, Inc., pp. 2-14 and 4-41.*

Jacoby, Mitch, Trading Places With Bisphenol A, Chemical and Engineering News, Dec. 15, 31 (2008).

"Bisphenol A: Toxic Plastics Chemical in Canned Food," accessed at http://web.archive.org/web/20101221233229/http://www.ewg.org/reports/bisphenola, published on Mar. 5, 2007, pp. 1-6.

Carwile, J.L., et al., "Polycarbonate Bottle Use and Urinary Bisphenol A Concentrations," Environ Health Perspect, vol. 117, No. 9, pp. 1368-1372 (2009).

Chemical Abstracts Accession No. 100:193662 & CAS Registry File RN 13410-58-7.

Chemical Abstracts Accession No. 101:25056 & CAS Registry File RN 80-04-6.

Danzel E., et al., "Biodegradation of Bisphenol A, Bisphenol F and Bisphenol S in Seawater," Int J Environ Res Public Health, vol. 6, No. 4, pp. 1472-1484 (2009).

Dodds, E.C., and Lawson, W., "Synthetic oestrogenic agents without the phenanthrene nucleus," Nature, vol. 137, No. 3476, pp. 996 (1936) Link: N/A.

International Search Report and Written Opinion for counterpart International Patent Application No. PCT/US2010/062333 mailed May 5, 2011.

Kitamura, S., et al., "Anti-thyroid hormonal activity of tetrabromobisphenol A, a flame retardant, and related compounds: Affinity to mammalian thyroid hormone receptor, and effect on tadpole metamorphosis," Life Science, vol. 76, pp. 1589-1601 (2005).

Kuroto-Niwa, R., et al., "Estrogenic activity of alkylphenols, bisphenol S, and their chlorinated derivatives using a GFP expression system," Environ Toxicol Pharmacol, vol. 19, No. 1, pp. 121-130 (2005).

Parez, P., et. al., "The estrogenicity of bisphenol A-related diphenylalkanes with various substituents at the central carbon and the hydroxy groups," Environmental Health Perspectives, vol. 106, No. 3, pp. 167-174 (1998).

Reid E.E. and Wilson, E., "The relation of estrogenic activity to structure in some 4,4'-dihydroxydiphenylmethanes," J. Am. Chem. Soc., vol. 66, No. 6, pp. 967-969 (1944).

International Search Report and Written Opinion dated May 5, 2011 in application No. PCT/US2010/062333.

* cited by examiner

SUBSTANCES FOR USE AS BISPHENOL A SUBSTITUTES

CROSS-REFERENCE TO RELATED APPLICATIONS

This Application is a U.S. National Stage Application under 35 U.S.C. §371 claiming the benefit of International Application No. PCT/US2010/062333, filed on Dec. 29, 2010.

BACKGROUND

Bisphenol A (hereinafter "BPA") has been commonly used in the preparation of containers, many of which are designed to hold food or beverages. However, it has been found that BPA is an endocrine-disrupting compound that is eluted from the food and beverage containers and absorbed into the foods or drinks within the containers. It has been found that BPA has severe adverse health effects. Therefore, there is a desire to eliminate BPA from food and beverage container products, and thereby there is a need for substance that can be used as a substitute for BPA.

DETAILED DESCRIPTION

Figure 1A:
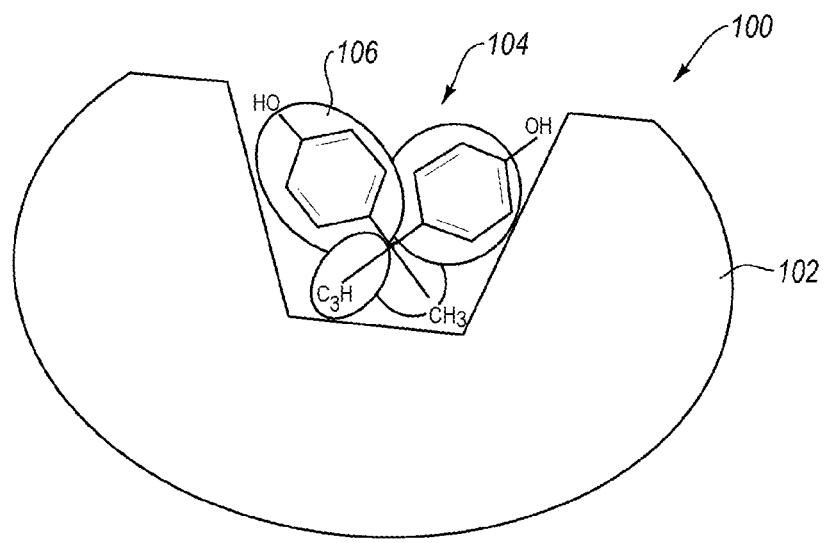
FIG. 1A includes a schematic representation of a BPA receptor having a ligand binding domain that receives and interacts with BPA.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Figure 1B:
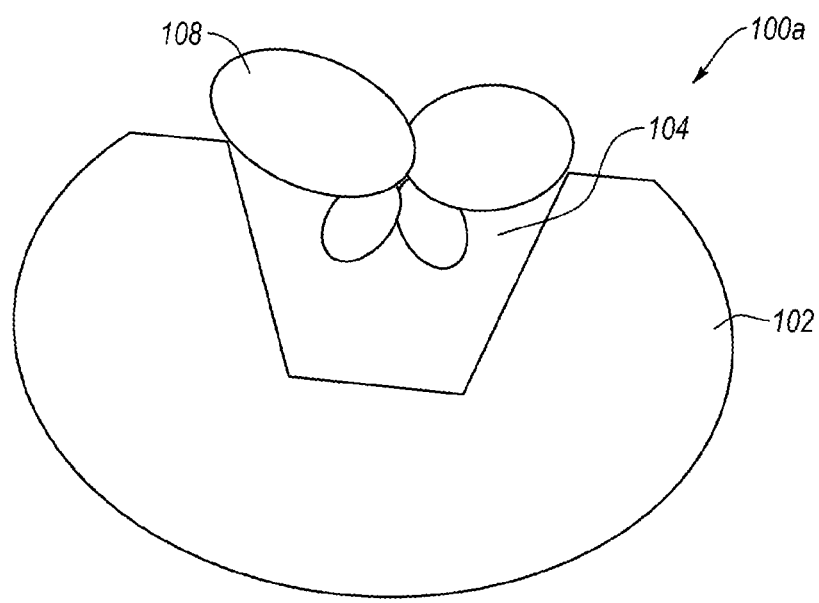
FIG. 1B includes a schematic representation of a BPA receptor having a ligand binding domain that does not receive or interact with a BPA substitute.

It is thought, without being bound thereto, that one or more receptors are involved in the BPA-induced endocrine (e.g., hormone) disruption process in the body. FIG. 1A includes a schematic representation of a BPA-receptor interaction 100. As shown, a BPA receptor 102 includes a ligand receptor domain 104 having a shape and size that receives BPA as a ligand. BPA has a spatial presence 106 that allows it to be received into the ligand receptor domain 104 of the BPA receptor 102. If the relationship between the receptor involved and BPA is a key-and-lock relationship (see FIG. 1A), it is possible that the uptake of BPA by receptors can be inhibited or will not occur if a BPA substitute has a different molecular shape or size (see FIG. 1B). As shown in FIG. 1B, a schematic representation of an inhibited receptor interaction 100a, where a BPA substitute 108 is designed such that it is sterically hindered from fitting within the ligand receptor domain 104 of the BPA receptor 102. It is thought that BPA substitutes 108 can be used to replace BPA in various industrial processes. Consequently, the adverse properties of BPA as an endocrine-disrupting compound will decrease if it is not used. The BPA substitutes 108 that do not interact with the BPA receptor 102 can avoid the adverse affect on health presented by BPA.

In accordance with BPA substitutes that are sterically hindered from entering into or interacting with a ligand receptor domain of a BPA receptor, the following substances and their derivatives can be used as BPA substitutes: BPA derivative having alkylation of at least one of the benzene rings in BPA; replacement of the propylene structure in BPA with another alkylene structure; and/or hydrogenated benzene rings (e.g., 2,2'-bis(4-hydroxycyclohexyl)-propane) as a substitute for BPA.

A BPA substitute, as described herein, with a molecular shape and/or size that does not fit within a ligand receptor domain present invention, can be manufactured in conventional chemical synthesis plants. The BPA substitute can be provided as raw material for the large markets for polycarbonate resins (hereinafter "PC") or epoxy resins. Thus, the BPA substitutes described herein can be used in place of BPA in industrial and manufacturing processes.

Generally, the BPA substitute can be a derivative of BPA that has an altered shape and/or size that does not fit within or interact with a ligand binding domain of the BPA receptor. The BPA substitute can have a structure of Formula 1, Formula 2, Formula 3, Formula 4 or derivative thereof or stereoisomer thereof. The structures are shown below.

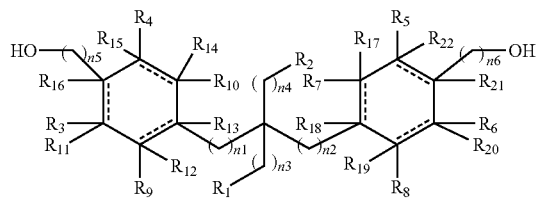

Formula 1

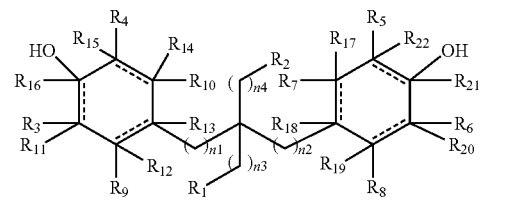

Formula 2

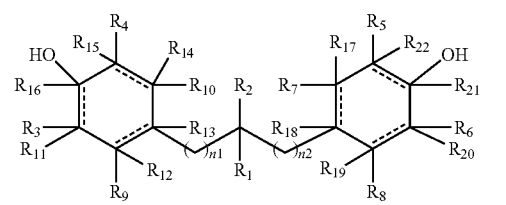

Formula 3

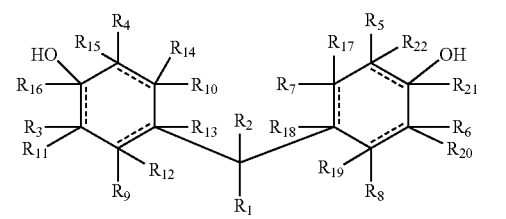

Formula 4

In Formulas 1, 2, 3, and 4, the structures are characterized by the following parameters. The rings are independently cyclic aliphatic or aromatic which is shown by the dashed lines. When the dashed lines are a bond, the BPA substitute includes one or more aromatic rings. When the dashed lines are nothing, the BPA substitute includes one or more aliphatic rings. When the rings are aromatic R11-R22 are nothing and one or more of R3-R6 is not hydrogen. Independently, R1-R22 can each include one or more of hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, or combinations thereof as well as other well known chemical substituents. The aliphatic groups can include n1-n6 each independently being about 0-20, about 1-10, or about 1-5.

The compounds represented by Formulas 1, 2, 3, or 4 can be characterized by one or more of the following: one or more of R1-R6 are not hydrogen; one or more of R1-R6 includes an aliphatic group; each of R1-R6 independently includes an aliphatic group, each of R1-R2 independently includes an aliphatic group; one or more of R1-R2 includes a methyl group; one or more of R3-R6 includes tert-butyl group; one or more R7-R22 are hydrogen; each of R7-R22 are hydrogen; each of n1-n4 independently is from 0 to 5; each of n1-n4 independently is from 0 to 2; each of n1-n4 is 0; each of n5-n6 independently is from 0 to 5; each of n5-n6 independently is from 0 to 2; or each of n5-n6 is 0. When the rings are aromatic, then R11-R22 are nothing.

In one embodiment, R1 and R2 are methyl, one or more of R3-R6 are tert-butyl, R7-R10 are hydrogen, the rings are aromatic, R11-R22 are nothing, and n1-n6 are 0.

In one embodiment, R1 and R2 are methyl, one or more of R3-R6 are tert-butyl, R7-R10 are hydrogen, the rings are aromatic, R11-R22 are nothing, one or more of n1-n2 are 1, and n3-n6 are 0.

In one embodiment, R1 and R2 are methyl, R3-R22 are hydrogen, and n1-n6 are 0.

In one embodiment, the BPA substitute can have a structure of Formula 1A, Formula 2A, Formula 3A, Formula 4A or derivative thereof or stereoisomer thereof, which can include the same parameters of R groups and n parameters as for Formula 1, Formula 2, Formula 3, or Formula 4.

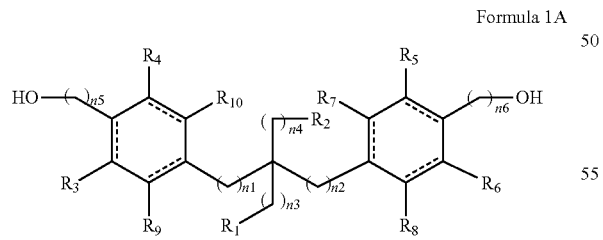

Formula 1A

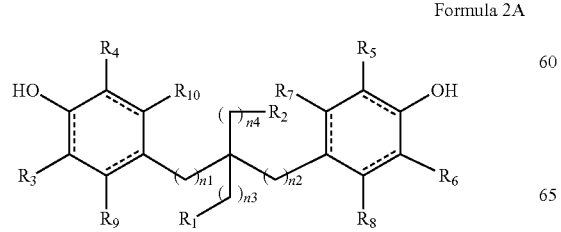

Formula 2A

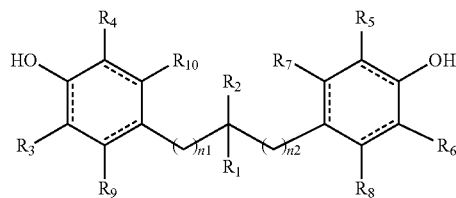

Formula 3A

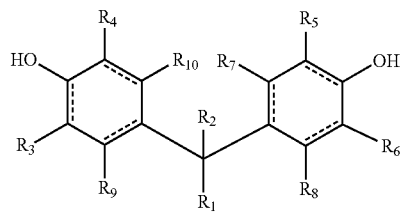

Formula 4A

In one embodiment, the BPA substitute can have a structure of Formula 1B, Formula 2B, Formula 3B, Formula 4B or derivative thereof or stereoisomer thereof, which can include the same parameters of R groups and n parameters as for Formula 1, Formula 2, Formula 3, or Formula 4.

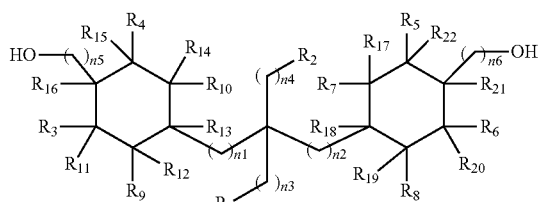

Formula 1B

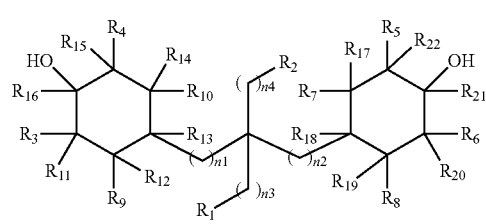

Formula 2B

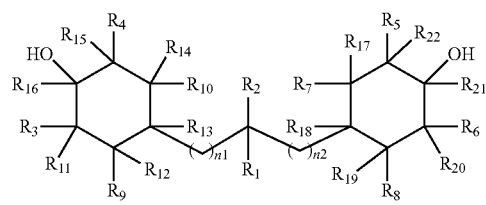

Formula 3b

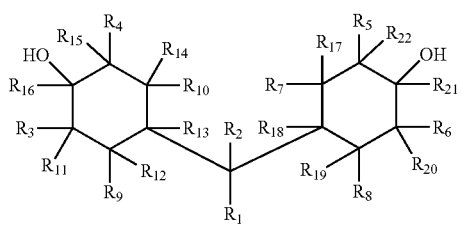

Formula 4B

In one embodiment, the BPA substitute can have a structure of Formula 1C, Formula 2C, Formula 3C, Formula 4C or derivative thereof or stereoisomer thereof, which can include the same parameters of R groups and n parameters as for Formula 1, Formula 2, Formula 3, or Formula 4. In one aspect, the BPA substitute specifically excludes 4,4'-isopropylidene-dicyclohexanol.

Formula 1C

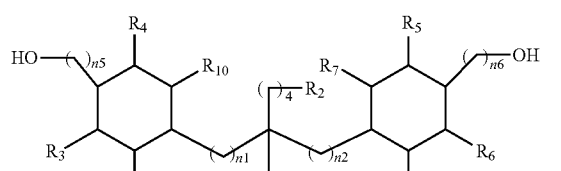

Formula 2C

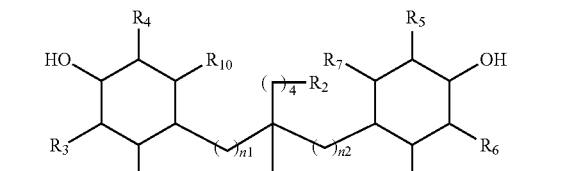

Formula 3C

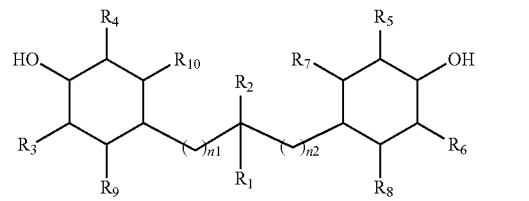

Formula 4C

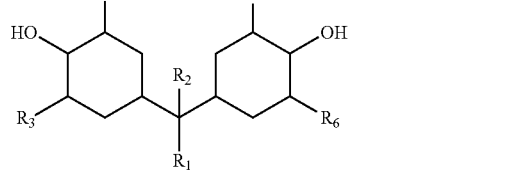

In one embodiment, the BPA substitute can have a structure of Formula 1D, Formula 2D, Formula 3D, Formula 4D or derivative thereof or stereoisomer thereof, which can include the same parameters of R groups and n parameters as for Formula 1, Formula 2, Formula 3, or Formula 4. It should be understood that BPA is specifically excluded from BPA substitutes.

Formula 1D

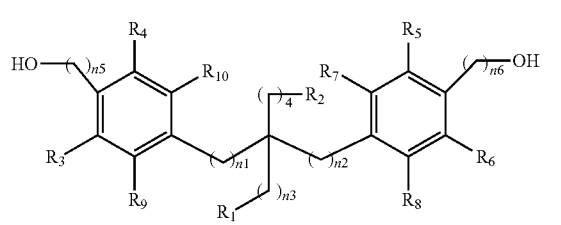

Formula 2D

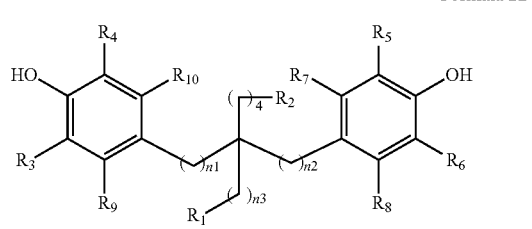

Formula 3D

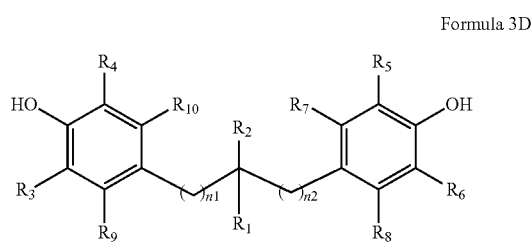

Formula 4D

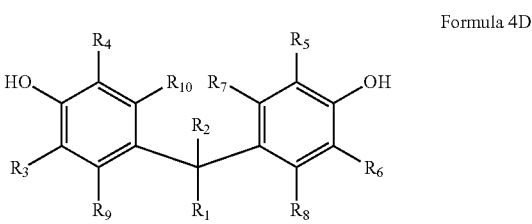

In one embodiment, a reaction scheme that can result in alkylation of a benzene ring present in a BPA substitute. In one example, the Friedel Craft reaction shown in reaction Scheme 1 is a synthesis technique that can produce embodiments of the invention. While not shown in Scheme 1, the starting reagent can be a derivative of BPA, where the reagent chemical structure results in the final product BPA substitute. Also, instead of tert-butyl bromine being used to derivatize the reagent, other halo-substituted substituents can be used. For example, the tert-butyl bromine can be replaced by a suitable reagent that can result in a BPA substitute as described and shown by the chemical formulas presented herein. Any of the several reaction products shown in the reaction Scheme 1 can be used as BPA substitutes; however, it may be necessary to perform chemical separation to obtain a particular embodiment of the BPA substitutes shown in Scheme 1.

Scheme 1

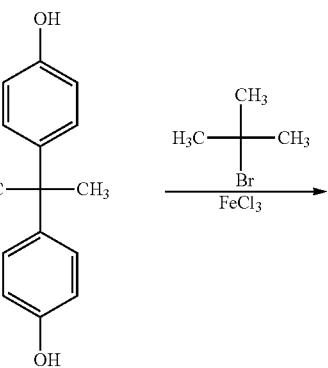

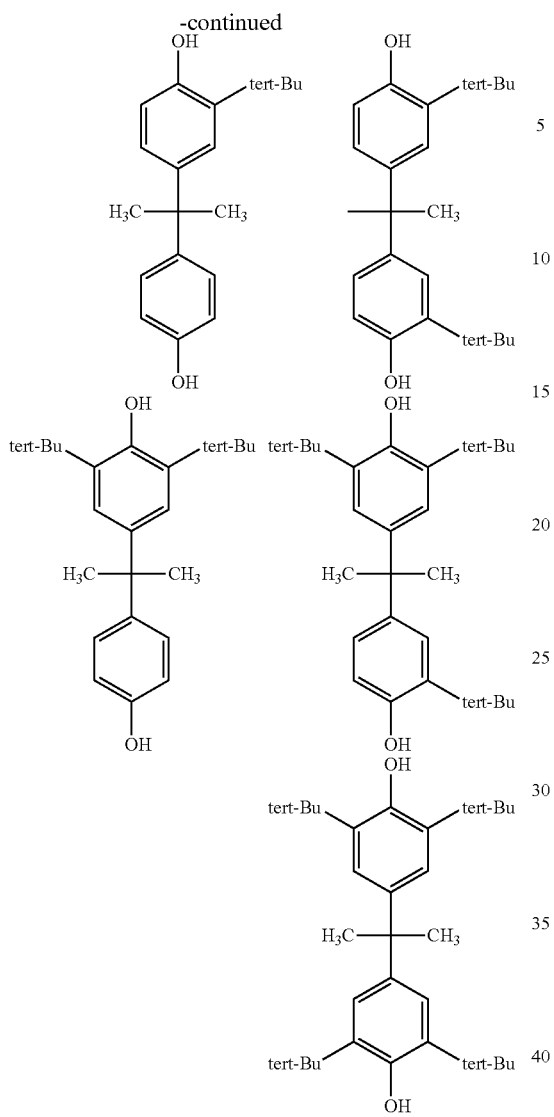

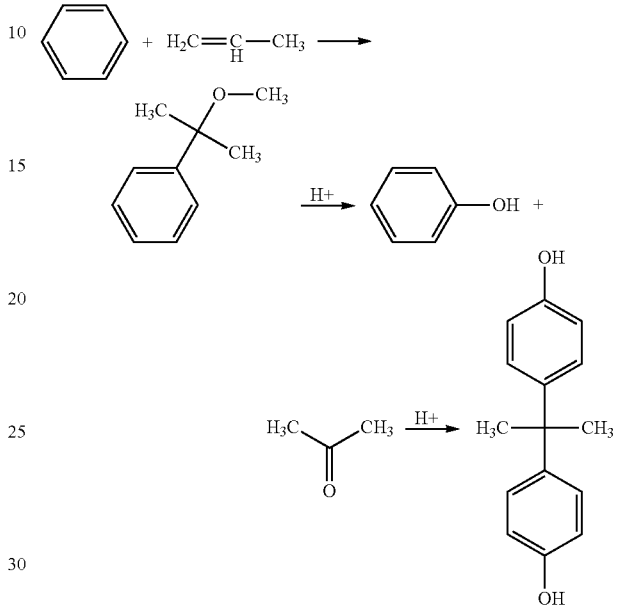

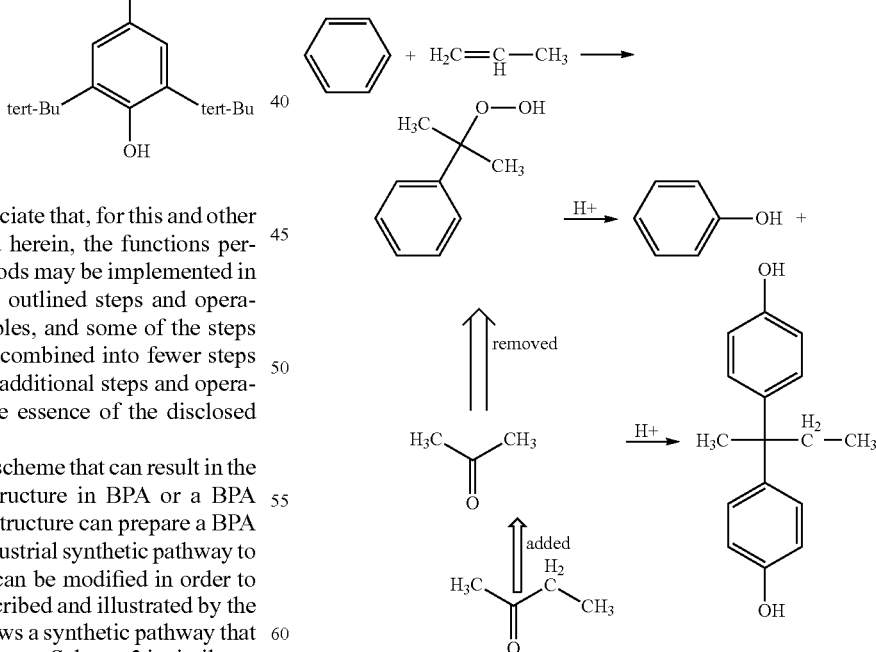

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

In one embodiment, a reaction scheme that can result in the replacement of the propylene structure in BPA or a BPA substitute with another alkylene structure can prepare a BPA substitute. Scheme 2 shows an industrial synthetic pathway to BPA. The reaction of Scheme 2 can be modified in order to obtain the BPA substitutes as described and illustrated by the chemical formulas. Scheme 3 shows a synthetic pathway that can be used to prepare BPA substitutes. Scheme 3 is similar to Scheme 2, however, methyl ethyl ketone is used instead of acetone, which results in the BPA substitute instead of BPA. As such, the synthetic pathways can be performed by removing the acetone that is produced by the cumene method of Scheme 2. The removed acetone can be replaced by other appropriate ketones (see Scheme 3). Accordingly, various ketone compounds having various alkyl or aliphatic groups can be selected depending on the desired BPA substitute product. In addition, aldehyde compounds having an alkyl or aliphatic group also can be used instead of ketone compounds in order to prepare BPA substitutes.

In one embodiment, the reaction scheme for producing the BPA substitute can modify Scheme 2 by replacing propylene, a raw material in the cumene method, with the appropriate olefin. Once the reagent that replaces propylene is selected for the desired BPA substitute, the synthesis can be performed without removing the acetone produced by the cumene method from the system and without adding other appropriate ketones (see Scheme 4). Scheme 4 is a synthetic pathway in which by replacing propylene with 1-butene, the illustrated BPA substitute can be prepared. Alternatively, the propylene can be replaced by some other alkylene to produce a BPA substitute. The double bond of the alkylene can be at a desired location with respect to the molecule in order to control the structure of the BPA substitute. In yet another alternative, the reaction in Scheme 4 can be started with the phenol and a desired ketone in order to prepare the desired BPA substitute. Scheme 4A is another synthetic pathway in which a BPA substitute can be prepared, and which is modified from standard production techniques for producing BPA. The reaction in Scheme 4A can be performed with any requisite starting material, either a different ketone or different ring structure in order to arrive at the BPA substitutes described herein. It should be understood that other BPA substitutes can be prepared by the general synthetic methods described herein by replacing the shown reagents with corresponding reagents that will result in the BPA substitutes described herein.

Scheme 4

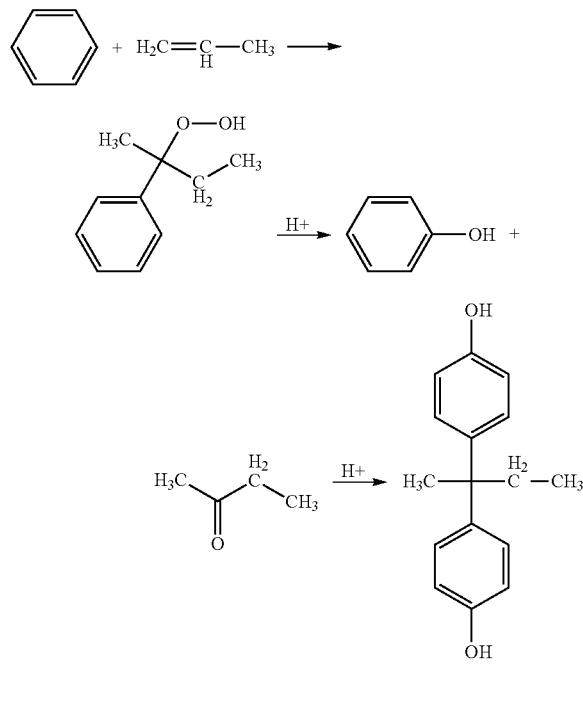

Scheme 4A

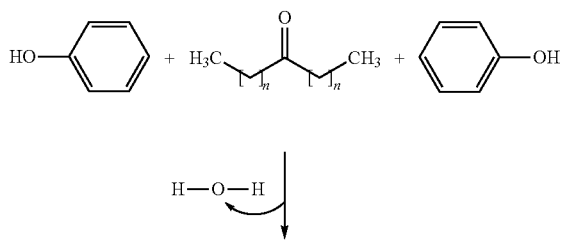

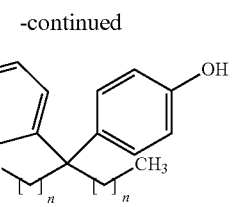

In one embodiment, a method of synthesizing a bisphenol-A substitute can include the method comprising: reacting a benzene or derivative thereof with an unsaturated aliphatic compound to form a reaction product that includes a benzyl group and an oxygen-oxygen bond; forming a phenol compound and a ketone from the reaction product; and forming a bisphenol-A substitute from the phenol compound and ketone. In one aspect, the benzene or derivative is benzene. In another aspect, the unsaturated aliphatic compound is a butanene. In yet another aspect, the ketone compound is a butyl ketone. In still another aspect, the phenol and ketone are formed from the reaction product by $H^+$. In another aspect, the BPA substitute is formed from the phenol and ketone by $H^+$. In an example, the BPA substitute can be formed by the reaction Scheme 4, wherein n8 is a positive integer. In one option, BPA is not formed.

In one embodiment, a method of synthesizing a bisphenol-A substitute can include: reacting two phenol molecules or derivatives thereof with an alkyl ketone compound; removing water; and forming a bisphenol-A substitute. In one aspect, the alkyl ketone is asymmetrical. In another aspect, the alkyl ketone is a butyl ketone. In one option, BPA is not formed.

In one embodiment, a reaction scheme for producing the BPA substitute can produce 2,2'-bis(4-hydroxycyclohexyl)-propane by hydrogenation is shown in Scheme 5. The reaction is Scheme 5 is hydrogenation of benzene in the BPA molecule. As such, other BPA substitutes having aromatic rings can be hydrogenated in order to produce the corresponding cyclohexyl BPA substitute. The reaction can be over Pd-supported carbon particles at 10 MPa and 250° C.

Scheme 5

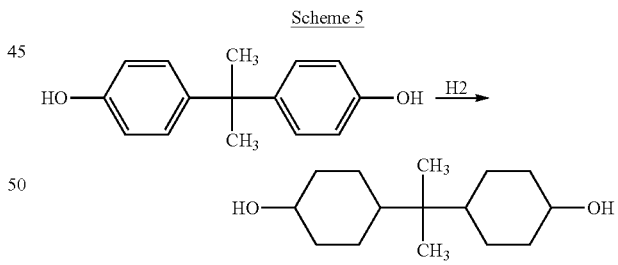

The reaction schemes shows can be used to prepare BPA substitutes having the formulas presented herein. These BPA substitutes can be used for preparing products traditionally prepared using BPA. However, the products prepared from the BPA substitutes can be less toxic and may be relatively safer compared to BPA.

In addition to the chemical structures of foregoing formulas, it has also been determined that 1,3-dihydroxy-2,2,4,4-tetramethyl-cyclobutane (hereinafter "DTC") and derivatives thereof may also be used as BPA substitutes. DTC has a molecular shape different from BPA and does not include two rings. DTC can be manufactured using conventional chemical synthesis techniques.

In one embodiment, DTC or derivative thereof can have a structure of Formula 5 or derivative thereof or stereoisomer thereof, and can be used as a BPA substitute.

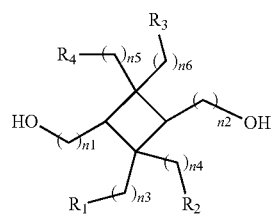

Formula 5

In Formula 5, the structures are characterized by the following parameters. R1-R4 each independently include one or more of hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, or combinations thereof. The aliphatic moieties can include n1-n6 each independently being about 0-20, about 1-10, or about 1-5. Also in Formula 5, one or more of R1-R4 is not hydrogen.

The compounds represented by Formula 5 can be characterized by one or more of the following: two or more or R1-R4 are not hydrogen; one or more of R1-R4 includes an aliphatic group; each of R1-R4 independently includes an aliphatic group; one or more of R1-R4 includes a methyl group; each of n1-n6 independently is from 0 to 10; each of n1-n6 independently is from 0 to 5; each of n1-n6 independently is from 0 to 2; or R1-R4 are each methyl and n1-n6 are each 0.

In one embodiment, the BPA substitute can have a structure of Formula 5A, Formula 5B, Formula 5C, Formula 5D or derivative thereof or stereoisomer thereof, which can include the same parameters of R groups and n parameters as for Formula 5. In one aspect, tetramethyl-1,3-cyclobutanediol is specifically excluded as a BPA substitute.

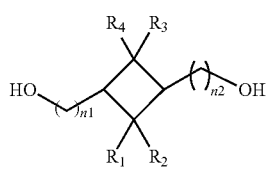

Formula 5A

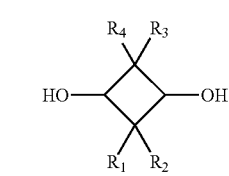

Formula 5B

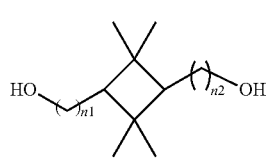

Formula 5C

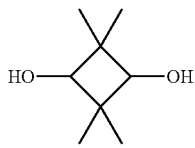

Formula 5D

In addition to the chemical structures of foregoing formulas, it has also been determined that 2,5-bis(hydroxymethyl)furan (hereinafter "BHF") and its derivatives can be used as BPA substitutes. BHF is a biomass-derived substance having a molecular shape different from BPA, and can be prepared by conventional chemical synthesis.

In one embodiment, BHF or derivative thereof can have a structure of Formula 6 or derivative thereof or stereoisomer thereof, and can be used as a BPA substitute.

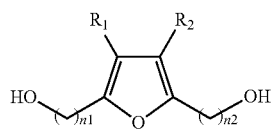

Formula 6

In Formula 6, the structures are characterized by the following parameters. R1-R2 each independently can include one or more of hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, or combinations thereof. The aliphatic moieties can include n1-n2 each independently being about 1-20, about 1-10, or about 1-5.

The compounds represented by Formula 6 can be characterized by one or more of the following: one or more of R1 or R2 is hydrogen; n1-n2 are independently 1-10; n1-n2 are independently 1-5; or n1-n2 are independently 1-2.

In one embodiment, the BPA substitute can have a structure of Formula 6A, Formula 6B, Formula 6C, or derivative thereof or stereoisomer thereof, which can include the same parameters of R groups and n parameters as for Formula 6. In one aspect, 2,5-bis(hydroxymethyl)furan is specifically excluded as a BPA substitute.

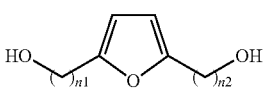

Formula 6A

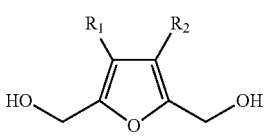

Formula 6B

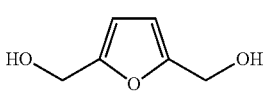

Formula 6C

The BHF can be obtained from biomass. In Scheme 6, the chemical reaction scheme to obtain BHF from biomass. For example, glucose from grape sugar can be used as the biomass to prepare BHF) is described. The compound on the far left side of Scheme 6 formula is glucose, the middle compound is 5-hydroxy-2-furfural, and the compound on the far right side is BHF. In the reaction of Scheme 6, the first reaction arrow (e.g., left arrow) indicates that the sugar is reacted with H+ and water to form the intermediate compound, which is then reacted (e.g., right arrow) with NaBH4 in order to produce BHF.

Scheme 6

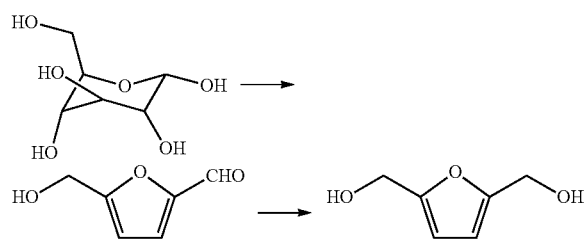

Epoxy Compositions

One of the traditional uses of BPA is in the preparation of epoxy compounds and compositions. Epoxies are thermosetting polymers formed from a reaction of an epoxide resin with an activator, where the activator interacts with the epoxide group of the epoxide resin to induce polymerization. Most common epoxy resins are produced from a reaction between epichlorohydrin and BPA. However, now the BPA can be replaced with the BPA substitutes described herein. The activator can be referred to as a hardener, and can include one or more amines such as monomers of polyamines. For example, triethylenetetramine (TETA) can be used as an activator. When BPA substitute and activator are mixed together in a reaction scheme, the amine groups can react with the epoxide groups to form covalent bonds. Each nitrogen group can react with an epoxide group, so that the resulting polymer is heavily crosslinked, and is thus rigid and strong. The process of polymerization that the BPA substitutes undergo can be referred to as "curing," and can be controlled through temperature and choice of BPA substitute and activator/hardener compounds. The epoxy reaction can take minutes to hours.

Epoxy materials can be used in coatings, adhesives and composite materials such as those using carbon fiber and fiberglass reinforcements. The chemistry of epoxies and the different BPA substitutes described herein can allow for a broad range of properties and applications. In general, epoxies prepared from BPA substitutes can have excellent adhesion, chemical and heat resistance, good-to-excellent mechanical properties, and good electrical insulating properties. The epoxies from BPA substitutes can be modified to have other properties, such as by combining electrically conductive particles (e.g., silver-filled epoxies) to produce electrically conductive epoxies. The BPA substitutes can be selected based on the end use for thermal insulation or thermal conductivity combined with high electrical resistance for electronics applications.

The epoxy compositions can include a BPA substitute and an epoxide, where the BPA substitute can react with epoxide to prepare a BPA substitute epoxide. The BPA substitute epoxide can have the epoxide moiety at one or both ends. Also, the epoxy composition can be devoid of BPA. The epoxide for reaction with the BPA substitute can include a leaving group that favors reaction with a hydroxy group of the BPA substitute. The leaving group on the epoxide can include a halogen, such as chlorine. An example of a suitable epoxide can include epichlorohydrin. Accordingly, a method of preparing a BPA substitute epoxide can include providing an epoxy composition having a BPA substitute and an epoxide, and reacting the BPA substitute with the epoxide so as to form the BPA substitute epoxide. The reaction can be conducted with NaOH and heat, and without BPA. The BPA substitute epoxide can be prepared by replacing BPA in standard reaction techniques with a BPA substitute as described herein.

The BPA substitute epoxide can be included in a two composition kit or system that when the two compositions are combined an epoxy is formed. For example only, the two-part epoxy kit can be used at a ratio of 1:1, 2:1; 3:1, 4:1, 5:1, 6:1, 7:1, 8:1, 9:1, 10:1, or vice versa or any other ratio, by volume mixing ratio, and can dry quickly once mixed providing a tough, UV resistant, protective coating that is extremely hard. The two-part epoxy kit can have low volatility, and can be cleaned up with water. The water cleanup makes the BPA substitute epoxy useful for factory cast iron, cast steel, cast aluminum applications. Also, the BPA substitute epoxy can be used without solvent, and thereby can have reduced flammability issues that are associated with solvent-borne coatings. The BPA substitute epoxy can be used in industrial and automotive applications, and are more heat resistant than latex-based and alkyd-based paints.

The BPA substitute epoxies are used as powder coatings for washers, driers and other articles of manufacture. Fusion Bonded Epoxy Powder Coatings (FBE) formed from the BPA substitute epoxies can be used for corrosion protection of steel pipes and fittings used in the oil and gas industry, potable water transmission pipelines (steel), concrete reinforcing rebar, and many other applications that are well known. The BPA substitute epoxy can be used as primers to improve the adhesion of automotive and marine paints, especially on metal surfaces where corrosion (e.g., rusting) resistance is important. Metal cans and containers can be coated with the BPA substitute epoxy to prevent rusting, especially for foods like tomatoes that are acidic. The BPA substitute epoxy resins are also used for high performance and decorative flooring applications especially terrazzo flooring, chip flooring, and colored aggregate flooring.

The BPA substitute epoxies can be used as structural adhesives or engineering adhesives, and can be used in applications that commonly use polyurethanes, acrylics, and cyanoacrylates. The BPA substitute epoxies can be used as adhesives in the construction of aircraft, automobiles, bicycles, boats, golf clubs, skis, snowboards, and other applications where high strength bonds are required. The BPA substitute epoxy adhesives can be used as adhesives for wood, metal, glass, stone, and some plastics. The BPA substitute epoxy adhesives can be made flexible or rigid, transparent or opaque or colored, and fast setting or slow setting.

The BPA substitute epoxies can be configured to be cured by exposure to ultraviolet light by including a UV crosslinking initiator, such as benzophenone, diphenoxy benzophenone, halogenated benzophenones, aminobenzophenones, fluorenone derivatives, anthraquinone derivatives, xanthone derivatives, thioxanthone derivatives, camphorquinone, and benzil. Such BPA substitute epoxies can be used in optics, fiber optics, optoelectronics, and dentistry.

The BPA substitute epoxies can be used in electronics for motors, generators, transformers, switchgear, bushings, and insulators. The BPA substitute epoxies can be used as electrical insulators, and can protect electrical components from short circuiting, dust and moisture. The BPA substitute epoxies can be used in overmolding integrated circuits, transistors and hybrid circuits, and making printed circuit boards.

The BPA substitute epoxide can include a structure of Epoxide Formula 1, Epoxide Formula 2, Epoxide Formula 3, Epoxide Formula 4 or derivative thereof or stereoisomer thereof. In one aspect, the BPA substitute epoxide can be devoid of a 4,4'-isopropylidenedicyclohexanol monomer.

1-5. Also, the BPA substitute epoxide can have n7 being 0 (zero) or any positive integer, such as greater than or equal to 1 or 2.

The BPA substitute epoxide can be characterized by one or more of the following: one or more or R1-R6 are not hydrogen; one or more of R1-R6 includes an aliphatic group; each of R1-R6 independently includes an aliphatic group; each of

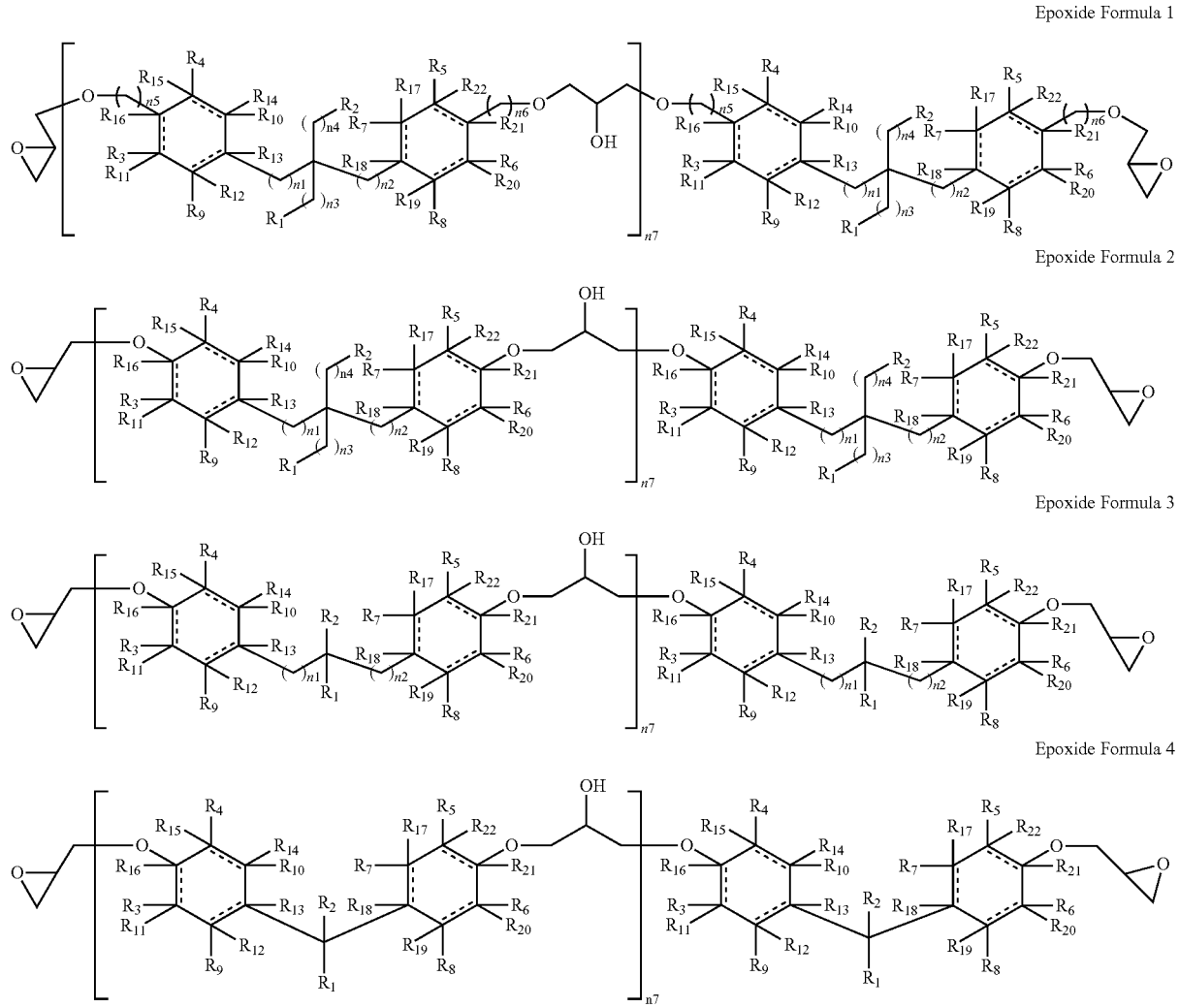

In Epoxide Formula 1, Epoxide Formula 2, Epoxide Formula 3, or Epoxide Formula 4, the BPA substitutes can be characterized by the following parameters. The rings can be independently cyclic aliphatic or aromatic, where the dashed lines may be bonds for an aromatic ring or may be nothing for cyclic aliphatic rings. When the rings are aromatic, R11-R22 are nothing and one or more of R3-R6 is not hydrogen. R1-R22 each independently can include one or more of hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, or combinations thereof. The aliphatic moieties can include n1-n6 each independently being about 0-20, about 1-10, or about R1-R2 independently includes an alkyl group; one or more of R1-R2 includes a methyl group; one or more of R3-R6 includes tert-butyl group; one or more R7-R22 are hydrogen; each of R7-R22 are hydrogen; each of n1-n4 independently is from 0 to 5; each of n1-n4 independently is from 0 to 2; each of n1-n4 is 0; each of n5-n6 independently is from 0 to 5; each of n5-n6 independently is from 0 to 2; or each of n5-n6 is 0. Also, when the rings are aromatic and R11-R22 are nothing.

In one embodiment, R1 and R2 are methyl, one or more of R3-R6 are tert-butyl, R7-R10 are hydrogen, the rings are aromatic, R11-R22 are nothing, and n1-n6 are 0.

In one embodiment, R1 and R2 are methyl, one or more of R3-R6 are tert-butyl, R7-R10 are hydrogen, the rings are aromatic, R11-R22 are nothing, one or more of n1-n2 are 1, and n3-n6 are 0.

In one embodiment, R1 and R2 are methyl, R3-R22 are hydrogen, and n1-n6 are 0.

In one embodiment, the BPA substitute epoxide can have a structure of Epoxide Formula 1A, Epoxide Formula 2A, Epoxide Formula 3A, Epoxide Formula 4A, or derivative thereof or stereoisomer thereof, which can include the same parameters of R groups and n parameters as for Epoxide Formula 1, Epoxide Formula 2, Epoxide Formula 3, or Epoxide Formula 4.

In one embodiment, the BPA substitute epoxide can have a structure of Epoxide Formula 1B, Epoxide Formula 2B, Epoxide Formula 3B, Epoxide Formula 4B, or derivative thereof or stereoisomer thereof, which can include the same parameters of R groups and n parameters as for Epoxide Formula 1, Epoxide Formula 2, Epoxide Formula 3, or Epoxide Formula 4.

Epoxide Formula 1A

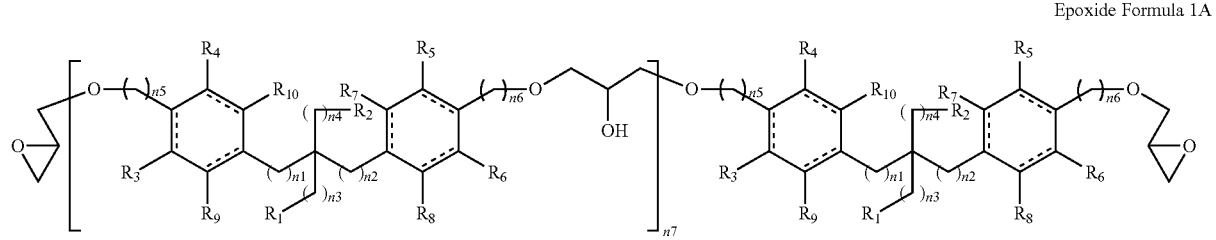

Epoxide Formula 2A

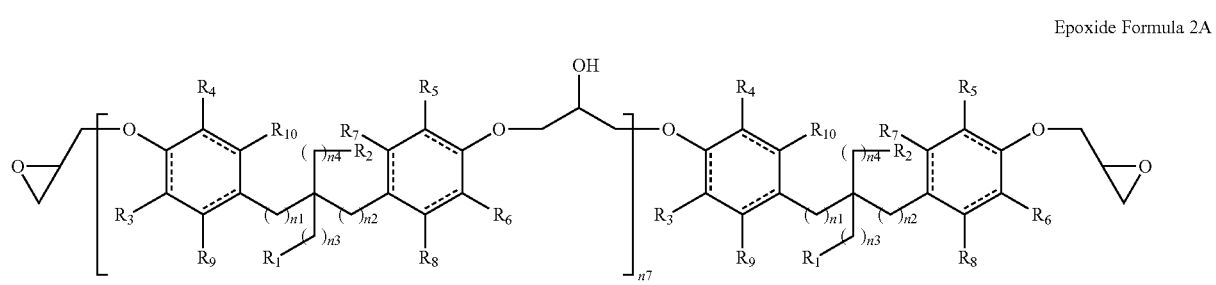

Epoxide Formula 3A

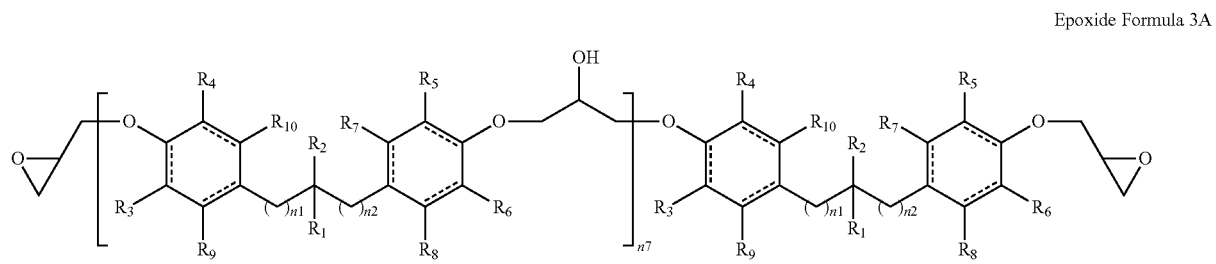

Epoxide Formula 4A

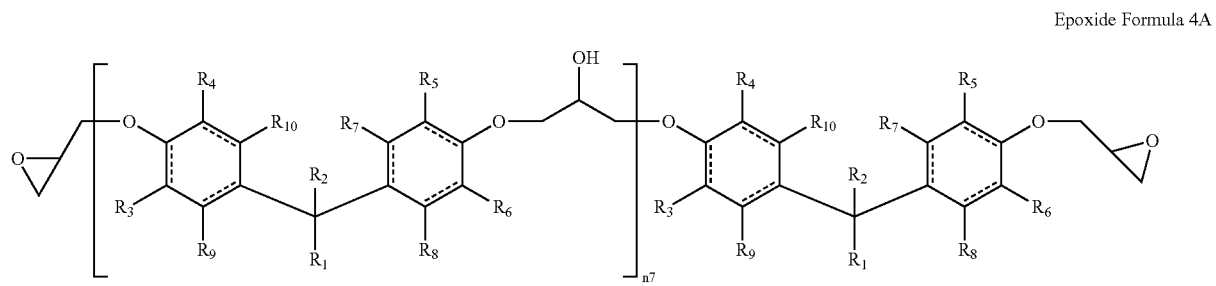

Epoxide Formula 1B

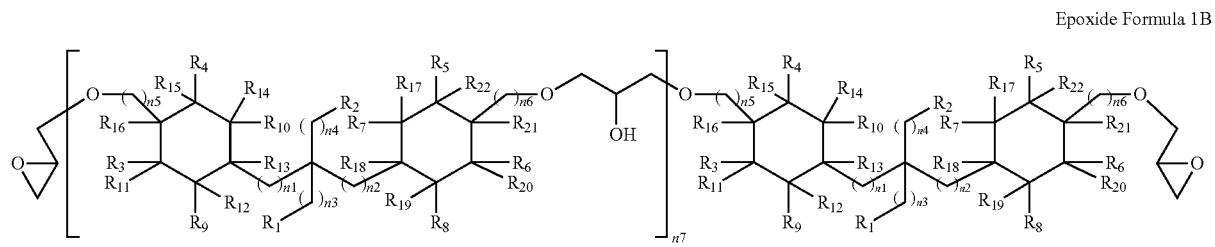

Epoxide Formula 2B

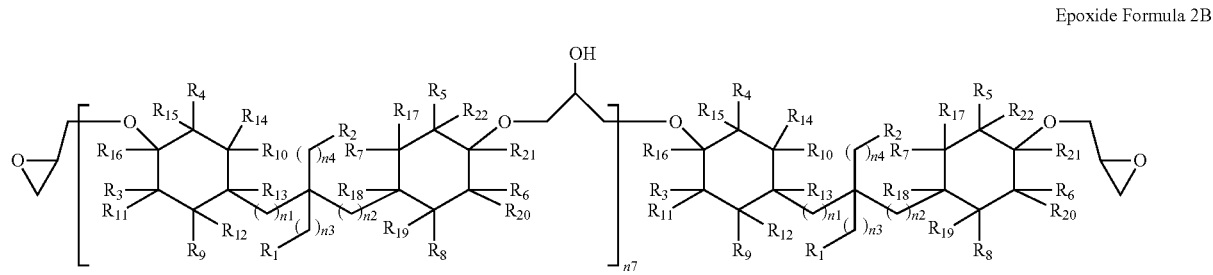

Epoxide Formula 3B

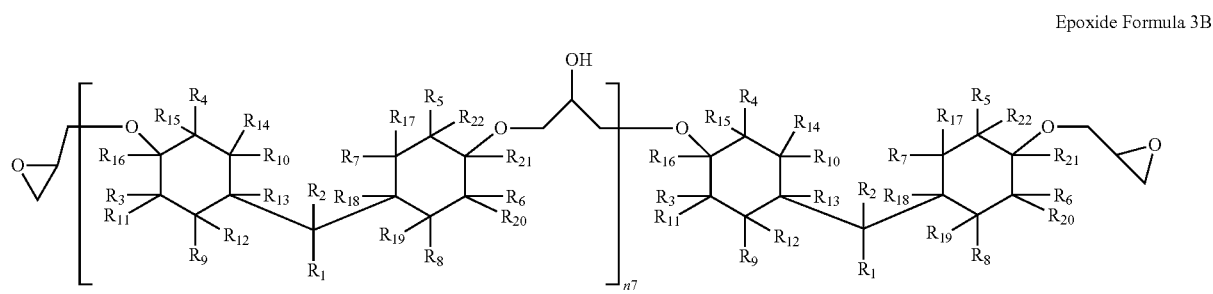

Epoxide Formula 4B

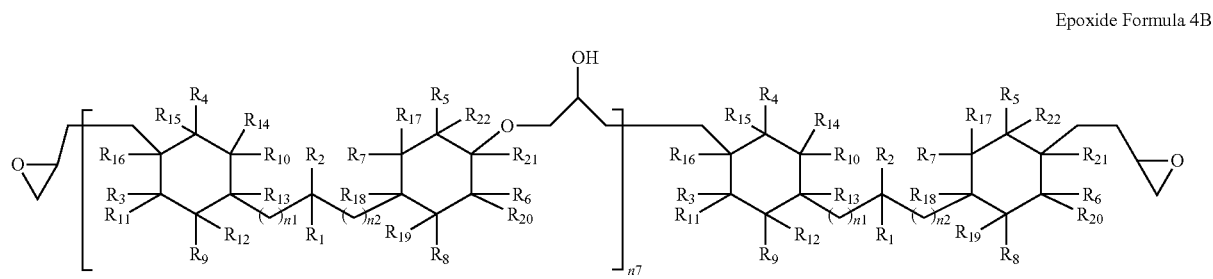

In one embodiment, the BPA substitute epoxide can have a structure of Epoxide Formula 1C, Epoxide Formula 2C, Epoxide Formula 3C, Epoxide Formula 4C, or derivative thereof or stereoisomer thereof, which can include the same parameters of R groups and n parameters as for Epoxide Formula 1, Epoxide Formula 2, Epoxide Formula 3, or Epoxide Formula 4.

Epoxide Formula 1C

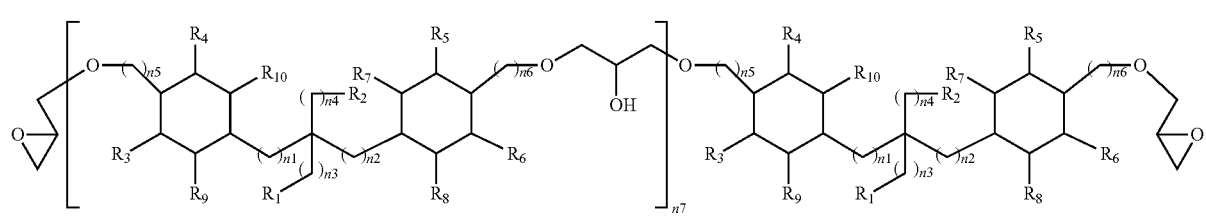

Epoxide Formula 2C

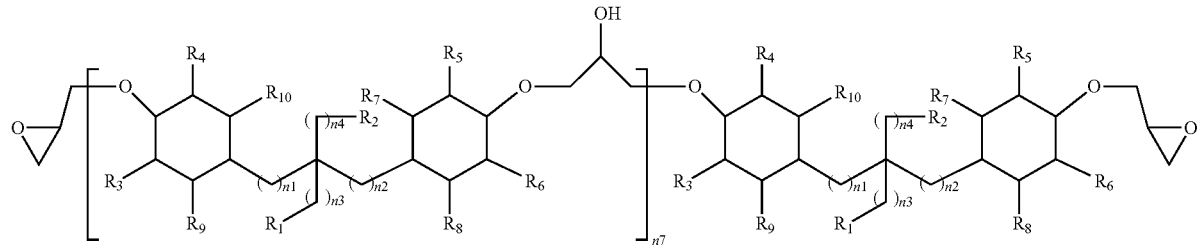

Epoxide Formula 3C

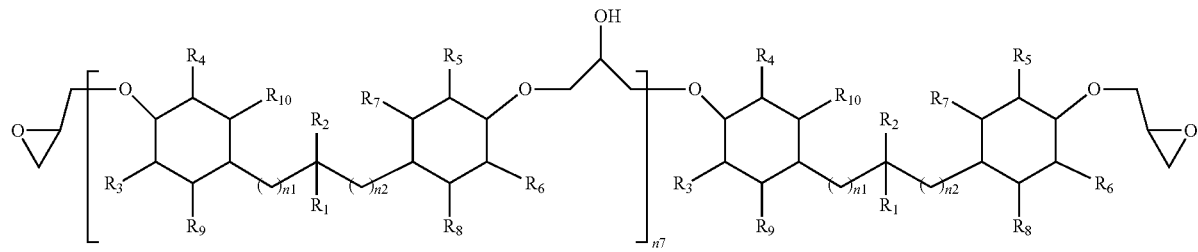

Epoxide Formula 4C

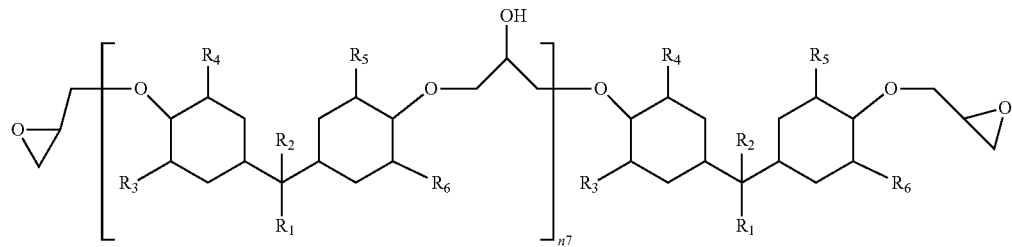

In one embodiment, the BPA substitute epoxide can have a structure of Epoxide Formula 1D, Epoxide Formula 2D, Epoxide Formula 3D, Epoxide Formula 4D, or derivative thereof or stereoisomer thereof, which can include the same parameters of R groups and n parameters as for Epoxide Formula 1, Epoxide Formula 2, Epoxide Formula 3, or Epoxide Formula 4.

Epoxide Formula 1D

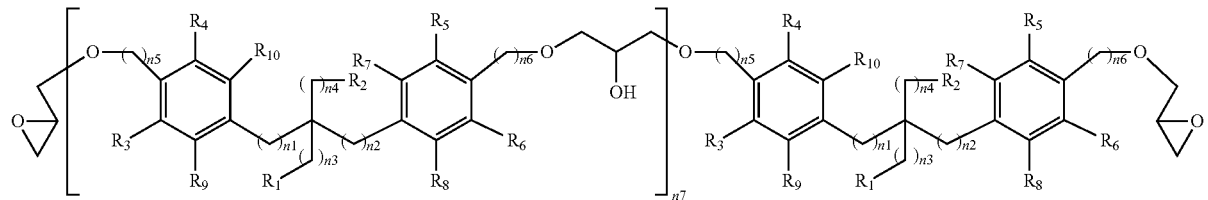

Epoxide Formula 2D

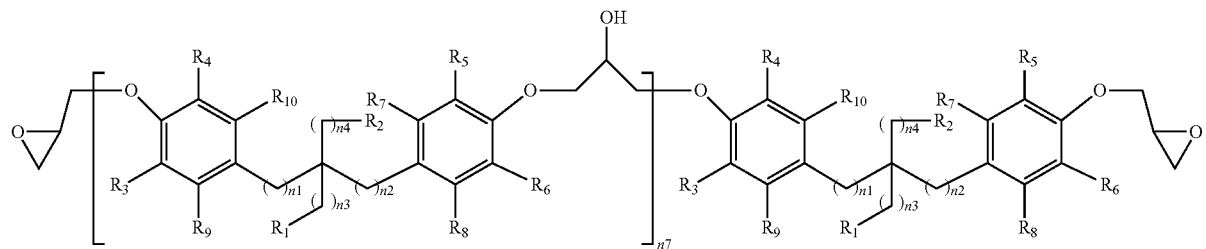

Epoxide Formula 3D

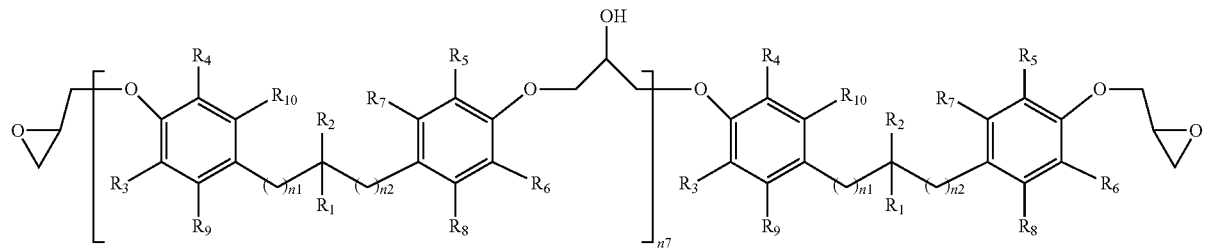

Epoxide Formula 4D

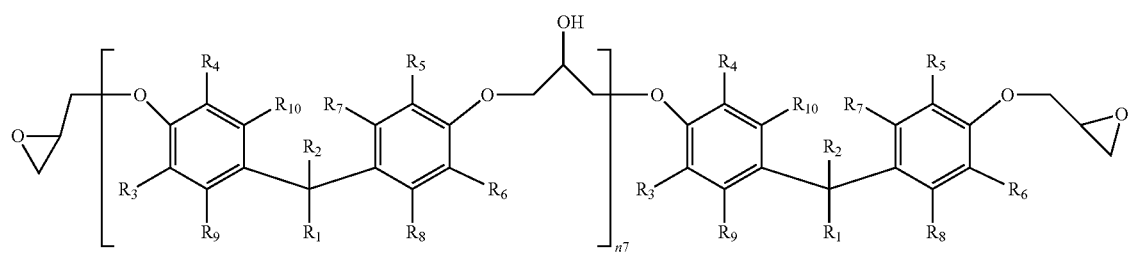

In one embodiment, the BPA substitute epoxide can have a structure of Epoxide Formula 5 or derivative thereof or stereoisomer thereof. In one aspect, the BPA substitute epoxide can be devoid of a tetramethyl-1,3-cyclobutanediol monomer.

Epoxide Formula 5

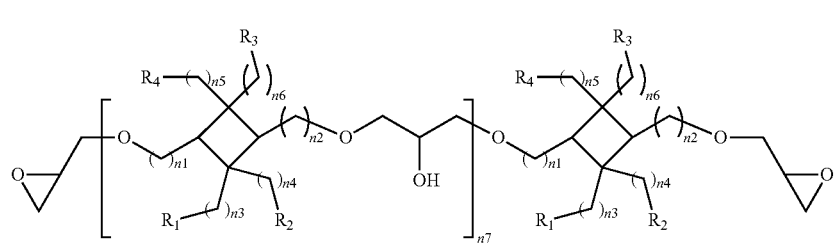

In Epoxide Formula 5, the BPA substitutes can be characterized by the following parameters. R1-R4 each independently can include one or more of hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, or combinations thereof. In the aliphatic moiety n1-n6 each independently are about 0-20, about 1-10, or about 1-5. Also, the BPA substitute epoxide can have n7 being 0 (zero) or any positive integer, such as greater than or equal to 1 or 2. Additionally, one or more of R1-R4 is not hydrogen.

The BPA substitute epoxide can be characterized by one or more of the following: one or more or R1-R4 are not hydrogen; one or more of R1-R4 includes an aliphatic group; each of R1-R4 independently includes an aliphatic group; one or more of R1-R4 includes a methyl group; each of n1-n6 independently is from 0 to 10; each of n1-n6 independently is from 0 to 5; each of n1-n6 independently is from 0 to 2. In one example, R1-R4 are each methyl and nα-n6 are each 0.

In one embodiment, the BPA substitute epoxide can have a structure of Epoxide Formula 5A, Epoxide Formula 5B, Epoxide Formula 5C, Epoxide Formula 5D, or derivative thereof or stereoisomer thereof. The BPA substitute epoxide of Epoxide Formula 5A, Epoxide Formula 5B, Epoxide Formula 5C, Epoxide Formula 5D, can include the same parameters of R groups and n parameters as for Epoxide Formula 5.

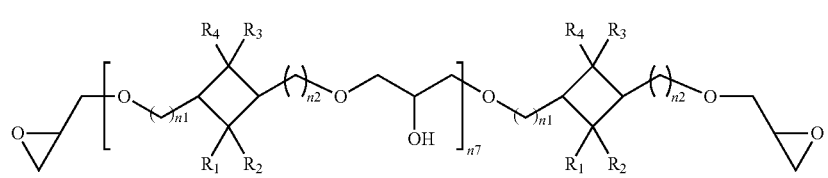

Epoxide Formula 5A

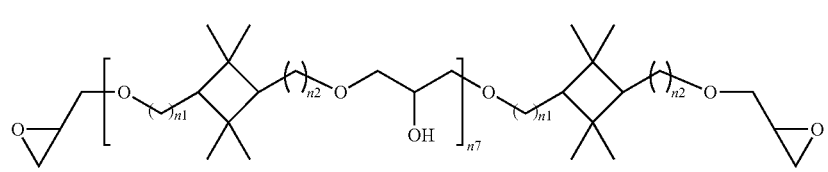

Epoxide Formula 5B

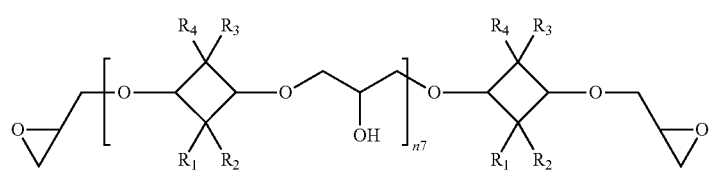

Epoxide Formula 5C

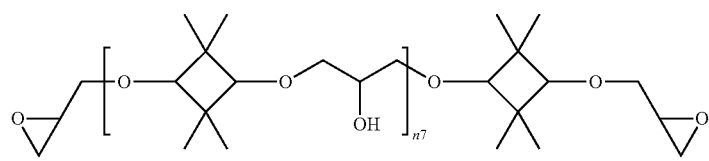

Epoxide Formula 5D

In one embodiment, the BPA substitute epoxide can have a structure of Epoxide Formula 6 or derivative thereof or stereoisomer thereof. In one aspect, the BPA substitute epoxide can be devoid of a bishydroxymethyl furan monomer.

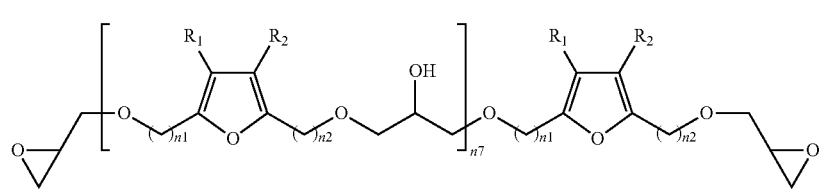

Epoxide Formula 6

In Epoxide Formula 5, the BPA substitutes can be characterized by the following parameters. R1-R2 each independently can include one or more of hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, or combinations thereof. In the aliphatic moiety n1-n6 each independently are about 0-20, about 1-10, or about 1-5. Also, the BPA substitute epoxide can have n7 being 0 (zero) or any positive integer, such as greater than or equal to 1 or 2.

The BPA substitute epoxide can be characterized by one or more of the following: one or more of R1 or R2 is hydrogen; n1-n2 are independently 1-10; n1-n2 are independently 1-5; or n1-n2 are independently 1-2.

In one embodiment, the BPA substitute epoxide can include a structure of Epoxide Formula 6A, Epoxide Formula 6B, Epoxide Formula 6C or derivative thereof or stereoisomer thereof, which can include the same parameters of R groups and n parameters as for Epoxide Formula 6.

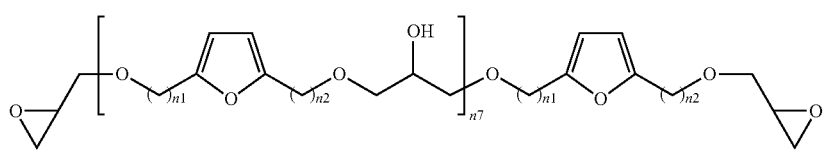

Epoxide Formula 6A

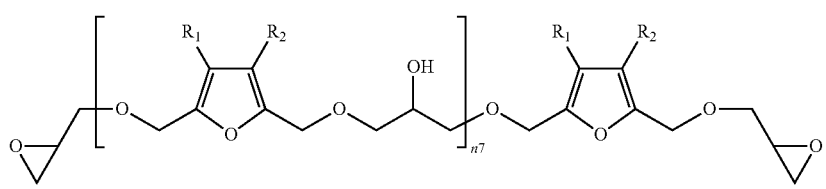

Epoxide Formula 6B

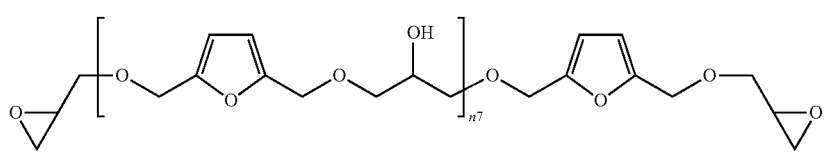

Epoxide Formula 6C

In one embodiment, an epoxy kit can be provided. The epoxy kit can include a BPA substitute epoxide, such as the epoxides of the epoxide formulas. The epoxy kit can also include an activator (also referred to as a hardener for epoxies) or hardener that reacts with the BPA substitute epoxide for polymerization or crosslinking. The activator can be a monomer having an amine. An example of an activator can include triethylenetetramine (TETA). The epoxy kit can include the epoxide in one composition and the activator in a different composition. The kit can also be devoid of BPA. The compositions of the kit can include one or more of the following: a colorant; a fiber; mineral fillers (e.g., talc, alumina, silica); viscosity reducers; solvent; thickeners; accelerators; adhesion promoters; or an electrically-conductive substance.

In one embodiment, an epoxy composition can be provided. The epoxy composition can include a BPA substitute epoxide, such as the epoxides of the epoxide formulas. The epoxy composition can also include an activator (also referred to as a hardener for epoxies) or hardener that reacts with the BPA substitute epoxide for polymerization or crosslinking. The activator can be a monomer having an amine. An example of an activator can include triethylenetetramine (TETA). The epoxy composition can also be devoid of BPA. The epoxy composition can include one or more of the following: a colorant; a fiber; mineral fillers (e.g., talc, alumina, silica); viscosity reducers; solvent; thickeners; accelerators; adhesion promoters; or an electrically-conductive substance. The epoxy composition can be configured for use as one of the following: a paint; a coating; a powder coating; a fusion bonded epoxy powder coating; a paint primer; an adhesive; or a composite having a carbon fiber or fiberglass.

In one embodiment, the epoxy kit and/or the epoxy composition can be used for manufacturing an article of manufacture. The article of manufacture can include a crosslinked epoxy formed from a bisphenol-A substitute epoxide having a structure as described herein. The article can be devoid of BPA. The article of manufacture includes one or more of the following: washer; dryer; pipes and/or pipe fittings; rebar; metal container; polycarbonate container; plastic container; food/beverage container; acidic product container; flooring; terrazzo flooring; chip flooring; colored aggregate flooring; adhesive for wood, metal, glass, stone, and/or plastic; fiber optic; optoelectronics; article mold; tool; motor; generator; transformer; switchgear; bushings; electric insulator; thermal insulator; integrated circuit; transistor; or printed circuit boards.

Polycarbonate Compositions

One of the traditional uses of BPA is in the preparation of polycarbonate reactants, compounds, and compositions. Polycarbonates are thermoplastic polymers that can be easily worked, molded, and thermoformed. Polycarbonates received their name because they are polymers containing carbonate groups (—O—(C=O)—O—). Traditionally, polycarbonate materials were produced by the reaction of BPA and phosgene ($COCl_2$). Now, a BPA substitute can be used for preparing polycarbonates. Preparing a polycarbonate from a BPA substitute can include treating the BPA substitute with a base, such as sodium hydroxide, and then reacting the product with phosgene which produces the polycarbonate having the BPA substitute.

The BPA substitute polycarbonates can be used in place of traditional polycarbonates formed from BPA. The BPA substitute polycarbonates can be highly transparent to visible light, and can be used in place of traditional glass, such as in windows, glasses, or optical elements. Also, this property allows for the BPA substitute polycarbonates to be used in data storage optical discs, such as CDs, DVDs, Blu-ray disks, or others. The BPA substitute can be used in different kinds of lenses, including automotive headlamp lenses, lighting lenses, sunglass/eyeglass, lenses, and safety glasses. The BPA substitute polycarbonates can be used in substantially the same applications and for substantially the same articles as described herein with regard to the epoxies.

In one embodiment, a polycarbonate composition can include a BPA substitute and phosgene (i.e., carbonyl dichloride, $COCl_2$). The polycarbonate composition can be devoid of BPA. Also, the composition can include a base, such as sodium hydroxide.

In one embodiment, a method of preparing a BPA substitute polycarbonate can include: providing a BPA polycarbonate; reacting the compound with a base so as to deprotonate hydroxyl groups of the BPA polycarbonate; reacting the deprotonated hydroxyl groups with phosgene to form a tetrahedral compound; forming a chloroformate from the tetrahedral compound and another compound; reacting the chloroformate with another deprotonated compound so as to form the BPA substitute polycarbonate. The base can be NaOH. The method can be conducted without bisphenol-A. The BPA substitute polycarbonate can be prepared by replacing BPA in standard reaction techniques with a BPA substitute as described herein.

In one embodiment, a BPA substitute polycarbonate can include a structure of Polycarbonate Formula 1, Polycarbonate Formula 2, Polycarbonate Formula 3, Polycarbonate Formula 4 or derivative thereof or stereoisomer thereof. In one aspect, the BPA substitute polycarbonate can be devoid of a 4,4'-isopropylidenedicyclohexanol monomer.

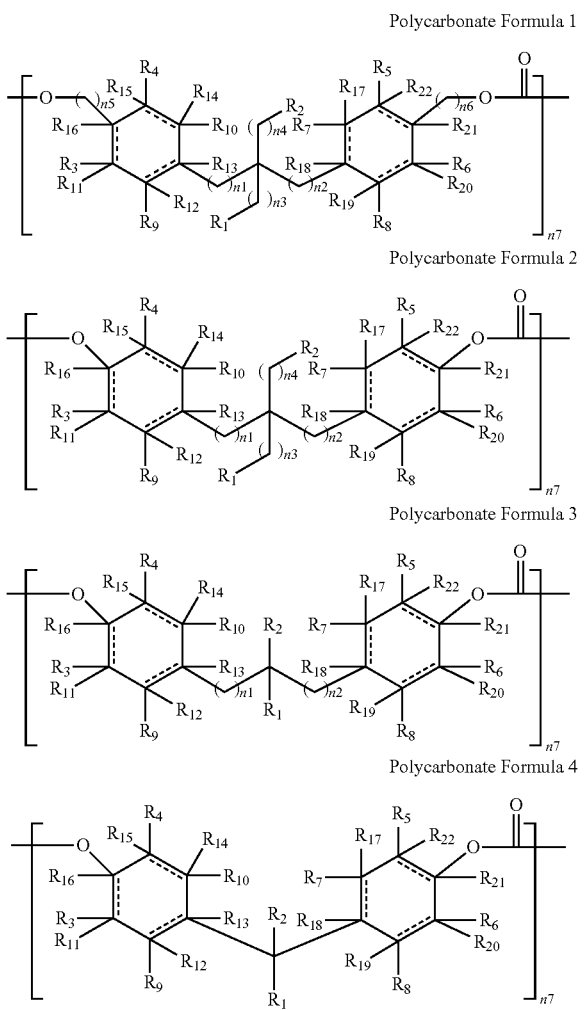

Polycarbonate Formula 1

Polycarbonate Formula 2

Polycarbonate Formula 3

Polycarbonate Formula 4

The BPA substitute polycarbonates of Polycarbonate Formula 1, Polycarbonate Formula 2, Polycarbonate Formula 3, Polycarbonate Formula 4 can be characterized by the following parameters. The rings can be independently cyclic aliphatic or aromatic, where the dashed lines may be bonds for an aromatic ring or may be nothing for cyclic aliphatic rings. When the rings are aromatic, R11-R22 are nothing and one or more of R3-R6 is not hydrogen. R1-R22 each independently can include one or more of hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, or combinations thereof. The aliphatic moieties can include n1-n6 each independently being about 0-20, about 1-10, or about 1-5. Also, the BPA substitute polycarbonate can have n7 being any positive integer, such as greater than or equal to 2.

The BPA substitute polycarbonate can be characterized by one or more of the following: one or more or R1-R6 are not hydrogen; one or more of R1-R6 includes an aliphatic group; each of R1-R6 independently includes an aliphatic group; each of R1-R2 independently includes alkyl groups; one or more of R1-R2 includes a methyl group; one or more of R3-R6 includes tert-butyl group; one or more R7-R22 are hydrogen; each of R7-R22 are hydrogen; each of n1-n4 independently is from 0 to 5; each of n1-n4 independently is from 0 to 2; each of n1-n4 is 0; each of n5-n6 independently is from 0 to 5; each of n5-n6 independently is from 0 to 2; or each of n5-n6 is 0. When the rings are aromatic, R11-R22 are nothing.

In one embodiment, R1 and R2 are methyl, one or more of R3-R6 are tert-butyl, R7-R10 are hydrogen, the rings are aromatic, R11-R22 are nothing, and n1-n6 are 0.

In one embodiment, R1 and R2 are methyl, one or more of R3-R6 are tert-butyl, R7-R10 are hydrogen, the rings are aromatic, R11-R22 are nothing, one or more of n1-n2 are 1, and n3-n6 are 0.

In one embodiment, R1 and R2 are methyl, R3-R22 are hydrogen, and n1-n6 are 0.

In one embodiment, the BPA substitute polycarbonate can have a structure of Polycarbonate Formula 1A, Polycarbonate Formula 2A, Polycarbonate Formula 3A, Polycarbonate Formula 4A, or derivative thereof or stereoisomer thereof, which can include the same parameters of R groups and n parameters as for Polycarbonate Formula 1, Polycarbonate Formula 2, Polycarbonate Formula 3, or Polycarbonate 4.

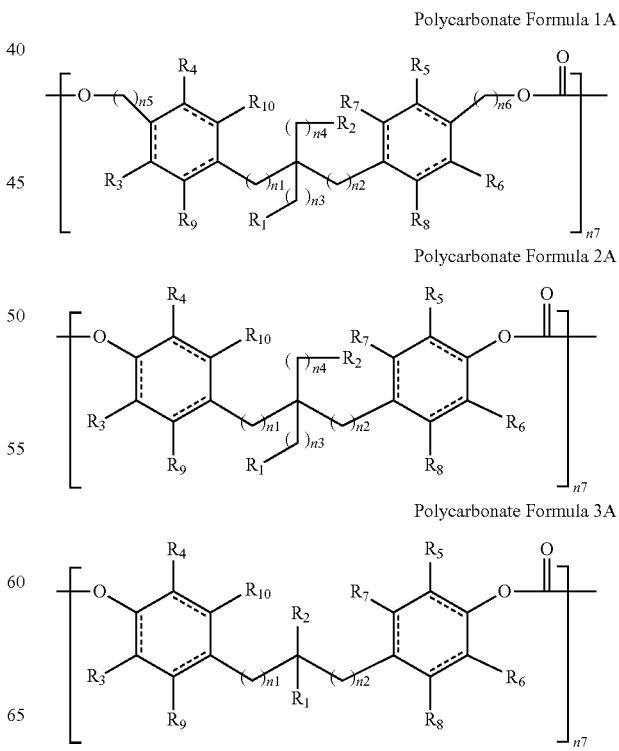

Polycarbonate Formula 1A

Polycarbonate Formula 2A

Polycarbonate Formula 3A

Polycarbonate Formula 4A

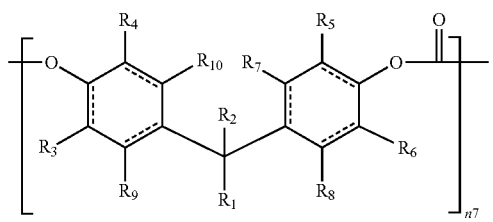

In one embodiment, the BPA substitute polycarbonate can have a structure of Polycarbonate Formula 1B, Polycarbonate Formula 2B, Polycarbonate Formula 3B, Polycarbonate Formula 4B, or derivative thereof or stereoisomer thereof, which can include the same parameters of R groups and n parameters as for Polycarbonate Formula 1, Polycarbonate Formula 2, Polycarbonate Formula 3, or Polycarbonate 4.

Polycarbonate Formula 1B

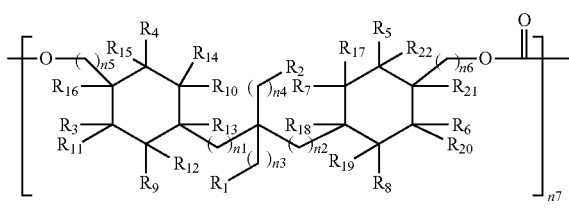

Polycarbonate Formula 2B

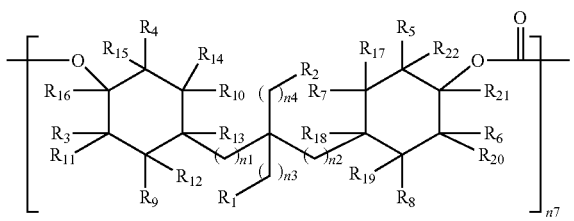

Polycarbonate Formula 3B

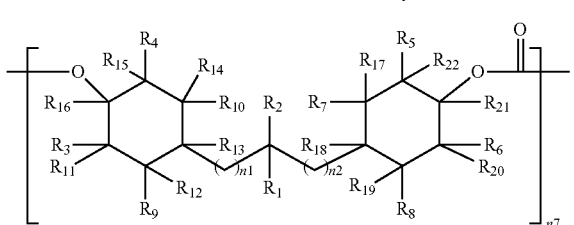

Polycarbonate Formula 4B

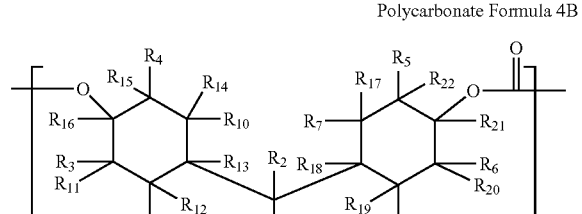

In one embodiment, the BPA substitute polycarbonate has a structure of Polycarbonate Formula 1C, Polycarbonate Formula 2C, Polycarbonate Formula 3C, Polycarbonate Formula 4C, or derivative thereof or stereoisomer thereof, which can include the same parameters of R groups and n parameters as for Polycarbonate Formula 1, Polycarbonate Formula 2, Polycarbonate Formula 3, or Polycarbonate 4.

Polycarbonate Formula 1C

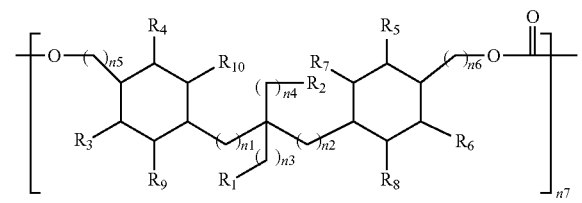

Polycarbonate Formula 2C

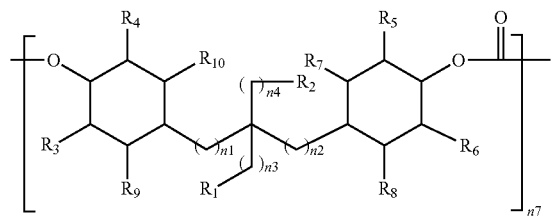

Polycarbonate Formula 3C

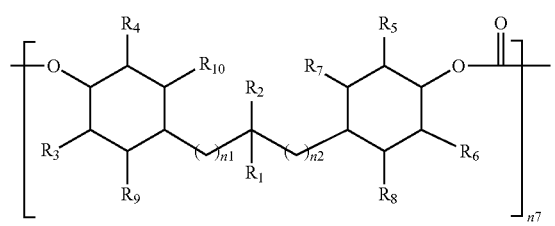

Polycarbonate Formula 4C

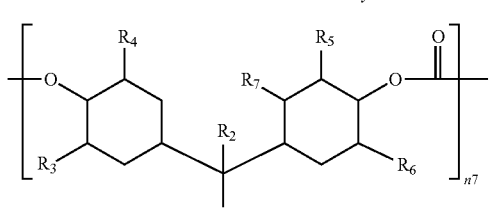

In one embodiment, the BPA substitute polycarbonate can have a structure of Polycarbonate Formula 1D, Polycarbonate Formula 2D, Polycarbonate Formula 3D, Polycarbonate Formula 4D, or derivative thereof or stereoisomer thereof, which can include the same parameters of R groups and n parameters as for Polycarbonate Formula 1, Polycarbonate Formula 2, Polycarbonate Formula 3, or Polycarbonate 4.

Polycarbonate Formula 1D

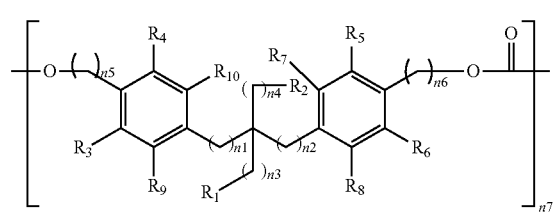

-continued

Polycarbonate Formula 2D

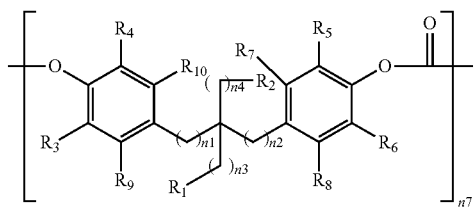

Polycarbonate Formula 3D

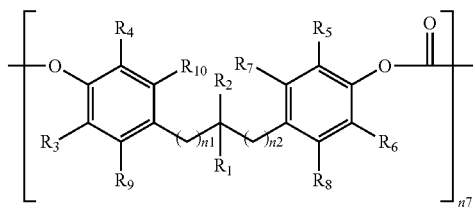

Polycarbonate Formula 4D

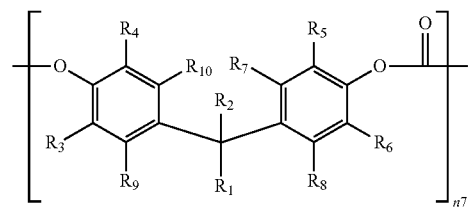

In one embodiment, a BPA substitute polycarbonate can include a structure of Polycarbonate Formula 5 or derivative thereof or stereoisomer thereof. In one aspect, the BPA substitute polycarbonate can be devoid of a tetramethyl-1,3-cyclobutanediol monomer.

Polycarbonate Formula 5

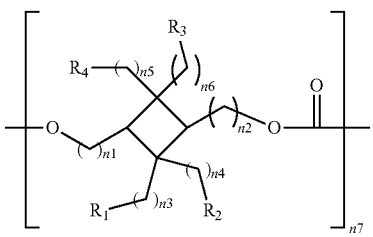

The BPA substitute polycarbonates of Polycarbonate Formula 5 can be characterized by the following parameters. R1-R4 each independently can include one or more of hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, or combinations thereof.

The aliphatic moieties can include n1-n6 each independently being about 0-20, about 1-10, or about 1-5. Also, the BPA substitute polycarbonate can have n7 being any positive integer greater than or equal to 2. Additionally, one or more of R1-R4 is not hydrogen.

The BPA substitute polycarbonate can be characterized by one or more of the following: two or more or R1-R4 are not hydrogen; one or more of R1-R4 includes an aliphatic group; each of R1-R4 independently includes an aliphatic group; one or more of R1-R4 includes a methyl group; each of n1-n6 independently is from 0 to 10; each of n1-n6 independently is from 0 to 5; each of n1-n6 independently is from 0 to 2; or R1-R4 are each methyl and n1-n6 are each 0.

In one embodiment, the BPA substitute polycarbonate can have a structure of Polycarbonate Formula 5A, Polycarbonate Formula 5B, Polycarbonate Formula 5C, Polycarbonate Formula 5D, or derivative thereof or stereoisomer thereof, which can include the same parameters of R groups and n parameters as for Polycarbonate Formula 5.

Polycarbonate Formula 5A

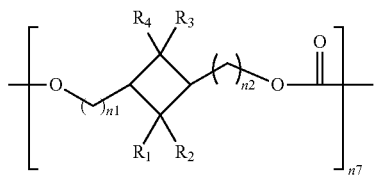

Polycarbonate Formula 5B

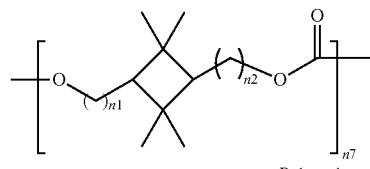

Polycarbonate Formula 5C

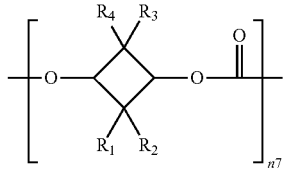

Polycarbonate Formula 5D

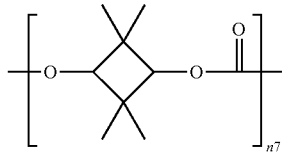

In one embodiment, a BPA substitute polycarbonate can have a structure of Polycarbonate Formula 6 or derivative thereof or stereoisomer thereof. In one aspect, the BPA substitute polycarbonate can be devoid of a bishydroxymethyl furan monomer.

Polycarbonate Formula 6

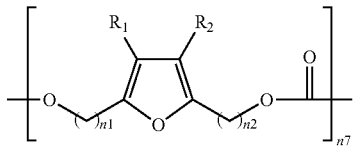

The BPA substitute polycarbonates of Polycarbonate Formula 6 can be characterized by the following parameters. R1-R2 each independently can include one or more of hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, or combinations thereof. The aliphatic moieties can include n1-n2 each independently being about 1-20, about 1-10, or about 1-5. Also, the BPA substitute polycarbonate can have n7 being any positive integer greater than or equal to 2.

The BPA substitute polycarbonate can be characterized by one or more of the following: one or more of R1 or R2 is hydrogen; one or more of R1 or R2 is not hydrogen; n1-n2 are independently 1-10; n1-n2 are independently 1-5; or n1-n2 are independently 1-2.

In one embodiment, the BPA substitute polycarbonate has a structure of Polycarbonate Formula 6A, Polycarbonate Formula 6B, Polycarbonate Formula 6C or derivative thereof or stereoisomer thereof, which can include the same parameters of R groups and n parameters as for Polycarbonate Formula 6.

Polycarbonate Formula 6A

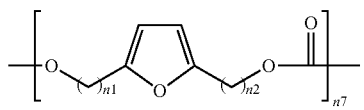

Polycarbonate Formula 6B

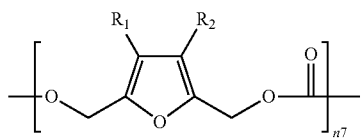

Polycarbonate Formula 6C

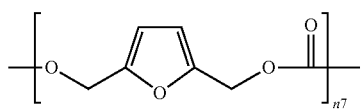

In one embodiment, a polycarbonate composition can have a BPA substitute polycarbonate as in one of the polycarbonate formulas. Such a polycarbonate composition can be devoid of bisphenol-A (BPA). The polycarbonate composition can be configured for one or more of the following: extrusion; injection molding; forming into a sheet; forming into a film; or machining into an article. The polycarbonate composition can be manufactured into an article of manufacture, such as one of the articles as follows: an article recited herein that can be prepared from an epoxy can be prepared from a polycarbonate; optical disc; food/beverage container; optical lens; eyeglass lens; sunglass lens; automotive headlamp lens; electronic device housing; toys; visual signs; or dielectric in high stability capacitors.

Polysulfone Compositions

One of the traditional uses of BPA is in the preparation of polysulfone reactants, compounds, and compositions. Polysulfones are thermoplastic polymers that have toughness and stability at high temperatures, and were commonly prepared from BPA. Now, BPA substitutes can be used to prepare BPA substitute polysulfones. Polysulfones can be used in applications in place of epoxies and polycarbonates. As such, uses of epoxies and polycarbonates as described herein are applicable to the BPA substitute polysulfones.

The BPA substitute polysulfones can be prepared with the same chemical synthesis techniques commonly used to prepare polysulfones with the BPA substitute being used in place of BPA. Generally, a BPA substitute can be reacted with a bis(4-chlorophenyl)sulfone to form a polyether.

In one embodiment, a BPA substitute polysulfone can have a structure of Polysulfone Formula 1, Polysulfone Formula 2, Polysulfone Formula 3, Polysulfone Formula 4 or derivative thereof or stereoisomer thereof. In one aspect, the BPA substitute polysulfone can be devoid of a 4,4'-isopropylidenedicyclohexanol monomer.

Polysulfone Formula 1

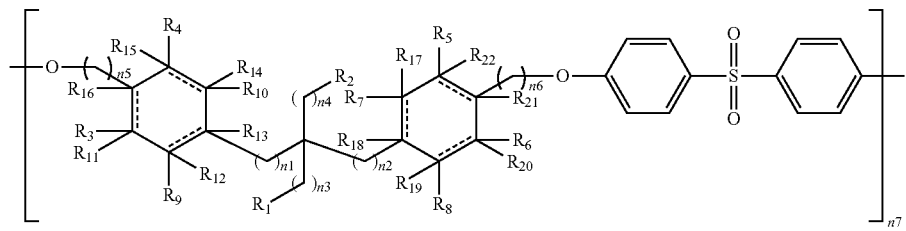

Polysulfone Formula 2

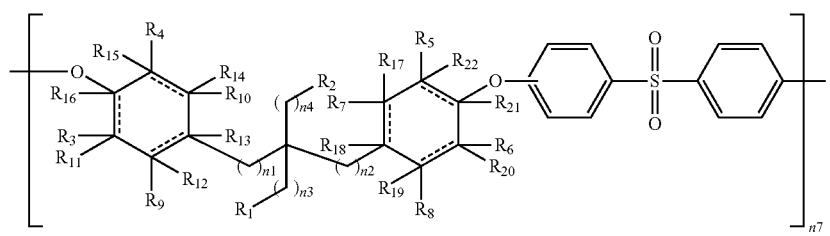

-continued

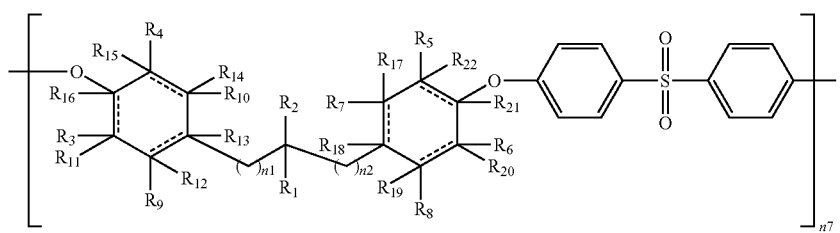

Polysulfone Formula 3

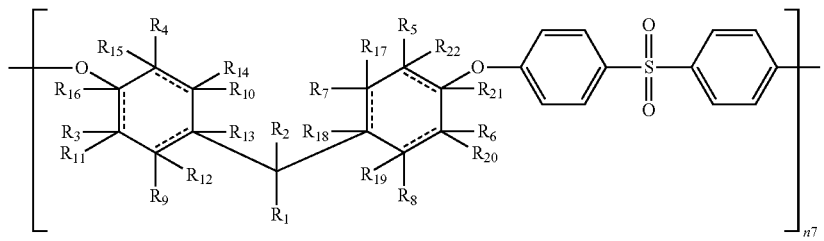

Polysulfone Formula 4

The BPA substitute polysulfone of Polysulfone Formula 1, Polysulfone Formula 2, Polysulfone Formula 3, Polysulfone Formula 4 can be characterized by the following parameters. The rings can be independently cyclic aliphatic or aromatic, where the dashed lines may be bonds for an aromatic ring or may be nothing for cyclic aliphatic rings. When the rings are aromatic, R11-R22 are nothing and one or more of R3-R6 is not hydrogen. R1-R22 each independently can include one or more of hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, or combinations thereof. The aliphatic moieties can include n1-n6 each independently being about 0-20, about 1-10, or about 1-5. Also, the BPA substitute polysulfone can have n7 being 0 (zero) or any positive integer.

The BPA substitute polysulfone can be characterized by one or more of the following: one or more or R1-R6 are not hydrogen; one or more of R1-R6 includes an aliphatic group; each of R1-R6 independently includes an aliphatic group; each of R1-R2 independently includes alkyl groups; one or more of R1-R2 includes a methyl group; one or more of R3-R6 includes tert-butyl group; one or more R7-R22 are hydrogen; each of R7-R22 are hydrogen; each of n1-n4 independently is from 0 to 5; each of n1-n4 independently is from 0 to 2; each of n1-n4 is 0; each of n5-n6 independently is from 0 to 5; each of n5-n6 independently is from 0 to 2; or each of n5-n6 is 0. When the rings are aromatic, R11-R22 are nothing.

In one embodiment, R1 and R2 are methyl, one or more of R3-R6 are tert-butyl, R7-R10 are hydrogen, the rings are aromatic, R11-R22 are nothing, and n1-n6 are 0.

In one embodiment, R1 and R2 are methyl, one or more of R3-R6 are tert-butyl, R7-R10 are hydrogen, the rings are aromatic, R11-R22 are nothing, one or more of n1-n2 are 1, and n3-n6 are 0.

In one embodiment, R1 and R2 are methyl, R3-R22 are hydrogen, and n1-n6 are 0.

In one embodiment, the BPA substitute polysulfone can have a structure of Polycarbonate Formula 1, where the BPA substitute portion can be any BPA substitute as described herein having Formulas 1A-1D, Formula 2A-2D, Formula 3A-D, Formula 4A-4D, or derivative thereof or stereoisomer thereof, which can include the same parameters of R groups and n parameters as for Formula 1, Formula 2, Formula 3, or Formula 4.

In one embodiment, the BPA substitute polysulfone can have a structure of Polysulfone Formula 5, Polysulfone Formula 5A, Polysulfone Formula 5B, Polysulfone Formula 5C, Polysulfone Formula 5D or derivative thereof or stereoisomer thereof. In one aspect, the BPA substitute polysulfone can be devoid of a tetramethyl-1,3-cyclobutanediol monomer.

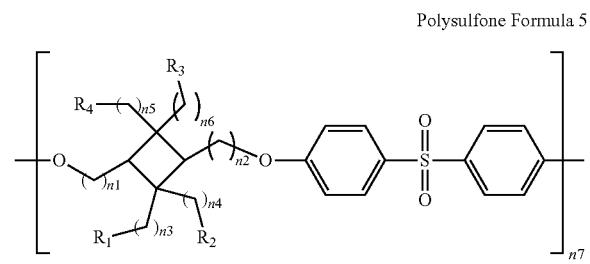

Polysulfone Formula 5

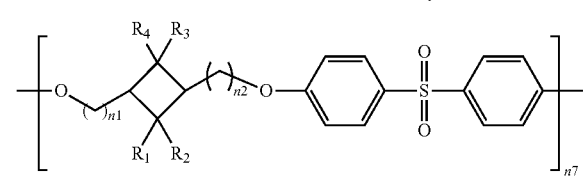

Polysulfone Formula 5A

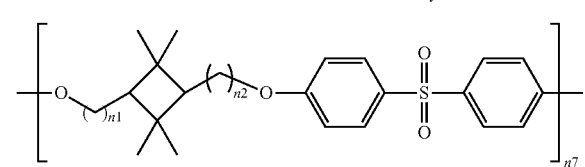

Polysulfone Formula 5B

Polysulfone Formula 5C

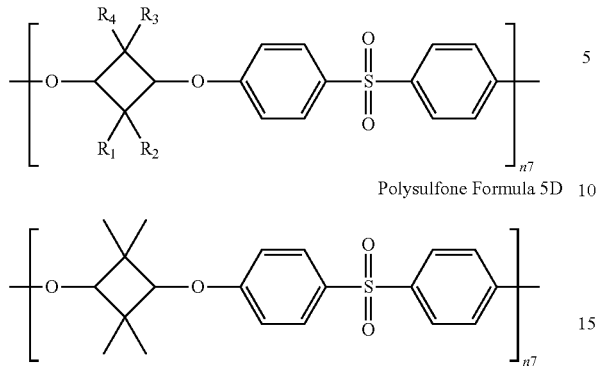

Polysulfone Formula 5D

The BPA substitute polysulfones of Polysulfone Formula 5, Polysulfone Formula 5A, Polysulfone Formula 5B, Polysulfone Formula 5C, or Polysulfone Formula 5D can be characterized by the following parameters. R1-R4 each independently can include one or more of hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, or combinations thereof. The aliphatic moieties can include n1-n6 each independently being about 0-20, about 1-10, or about 1-5. Also, the BPA substitute polysulfone can have n7 being 0 (zero) or any positive integer. Additionally, one or more of R1-R4 is not hydrogen.

The BPA substitute polysulfone can be characterized by one or more of the following: two or more or R1-R4 are not hydrogen; one or more of R1-R4 includes an aliphatic group; each of R1-R4 independently includes an aliphatic group; one or more of R1-R4 includes a methyl group; each of n1-n6 independently is from 0 to 10; each of n1-n6 independently is from 0 to 5; each of n1-n6 independently is from 0 to 2; or R1-R4 are each methyl and n1-n6 are each 0.

In one embodiment, a BPA substitute polysulfone can have a structure of Polysulfone Formula 6, Polysulfone Formula 6A, Polysulfone Formula 6B, Polysulfone Formula 6C, or derivative thereof or stereoisomer thereof. In one aspect, the BPA substitute polysulfone can be devoid of a bishydroxymethyl furan monomer.

Polysulfone Formula 6

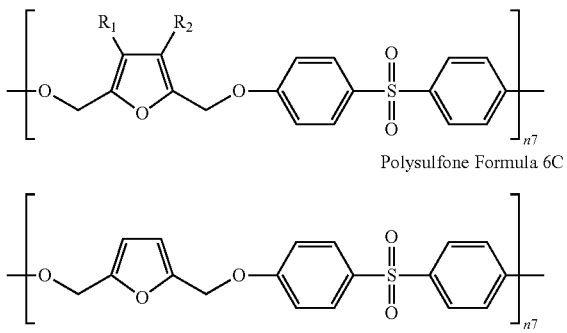

Polysulfone Formula 6A

Polysulfone Formula 6B

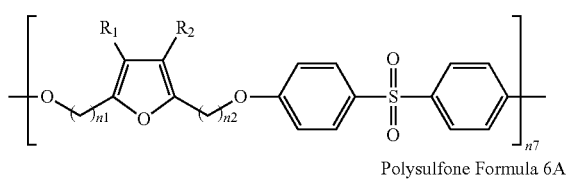

Polysulfone Formula 6C

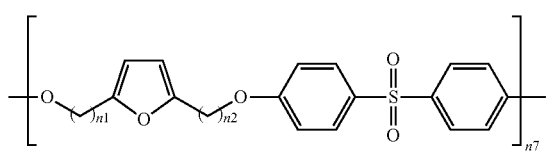

The BPA substitute polysulfones of Polysulfone Formula 6, Polysulfone Formula 6A, Polysulfone Formula 6B, or Polysulfone Formula 6C can be characterized by the following parameters. R1-R2 each independently can include one or more of hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, or combinations thereof. The aliphatic moieties can include n1-n2 each independently being about 1-20, about 1-10, or about 1-5. Also, the BPA substitute polysulfone can have n7 being 0 (zero) or any positive integer.

The BPA substitute polysulfone can be characterized by one or more of the following: one or more of R1 or R2 is hydrogen; one or more of R1 or R2 is not hydrogen; n1-n2 are independently 1-10; n1-n2 are independently 1-5; or n1-n2 are independently 1-2.

In one embodiment, a polysulfone composition can include a BPA substitute polysulfone as described herein. The BPA substitute polysulfone composition can be devoid of bisphenol-A. The BPA substitute polysulfone composition can be used to prepare articles of manufacture described herein in connection with epoxies and polycarbonates.

Additionally, any of the BPA substitutes described herein and represented by the chemical formulae can have any of the R groups independently selected from substituents selected from the group of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N$^+$≡C$^-$), cyanato (—O—C$^-$=N), isocyanato (—O—N$^+$≡C$^-$), isothiocyanato azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$S_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O—)), phospho (—$PO_2$), phosphino (—$PH_2$), derivatives thereof, and combinations thereof.

In one aspect, the BPA substitute polymers can have an average molecular weight of about 2000 daltons (Da), about 5000 Da, about 10,000 Da, about 15,000 Da, about 20,000 Da, about 25,000 Da, about 30,000 Da, about 35,000 Da, about 40,000 Da, about 45,000 Da, about 50,000 Da, about 60,000 Da, about 70,000 Da, about 80,000 Da, about 90,000 Da, about 100,000 Da, about 125,000 Da, about 150,000 Da, about 175,000 Da, about 200,000 Da, about 250,000 Da, about 300,000 Da, about 350,000 Da, about 400,000 Da, about 450,000 Da, about 500,000 Da, or any value therebetween.

The term "alkyl" or "aliphatic" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, or 1 to about 12 carbon atoms. The term "lower alkyl" intends an alkyl group of 1 to 6 carbon atoms. Substituents identified as "$C_1$-$C_6$ alkyl" or "lower alkyl" contains 1 to 3 carbon atoms, and such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The terms "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicoscnyl, tetracosenyl, and the like. Generally, although again not necessarily, alkenyl groups herein contain 2 to about 18 carbon atoms, or 2 to 12 carbon atoms. The term "lower alkenyl" intends an alkenyl group of 2 to 6 carbon atoms, and the specific term "cycloalkenyl" intends a cyclic alkenyl group, or having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, or 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein contain 1 to 3 carbon atoms, and such substituents contain 1 or 2 carbon atoms (i.e., methoxy and ethoxy).

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Examples of aryl groups contain 5 to 20 carbon atoms, and aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Examples of aryloxy groups contain 5 to 20 carbon atoms, and aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Examples of aralkyl groups contain 6 to 24 carbon atoms, and aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenyl cyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, and fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "hydrocarbyl" refers to univalent hydrocarbyl radicals containing 1 to about 30 carbon atoms, or 1 to about 24 carbon atoms, or 1 to about 18 carbon atoms, or about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, heteroatom-containing alkenyl, and heteroatom-containing aryl."

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. An epoxide comprising:
a structure of Epoxide Formula 1B, Epoxide Formula 2B, Epoxide Formula 3B, Epoxide Formula 4B or stereoisomer thereof:

Epoxide Formula 1B

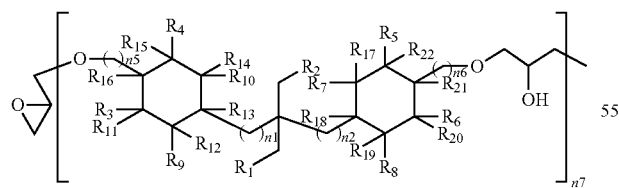

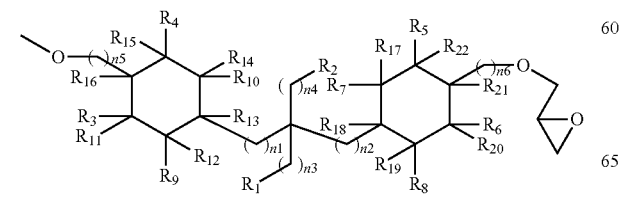

Epoxide Formula 2B

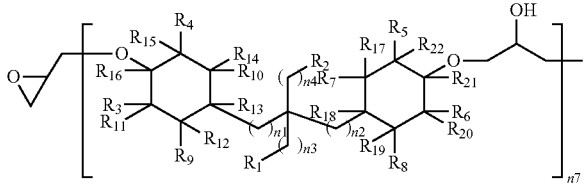

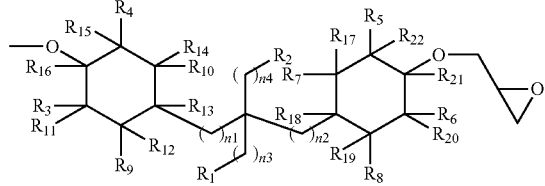

Epoxide Formula 3B

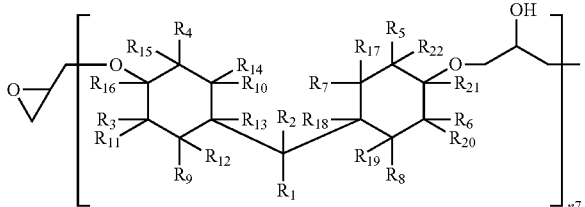

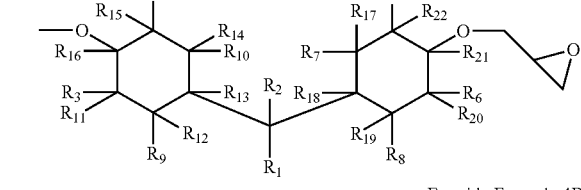

Epoxide Formula 4B

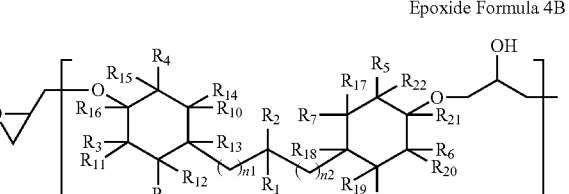

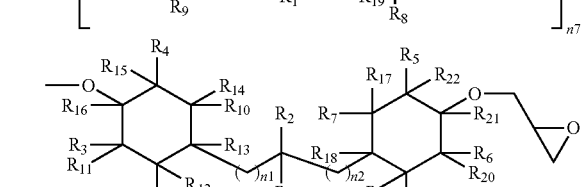

wherein:
R1-R2 each independently include one or more of amino acids, peptides, or polypeptides;
R3-R6 each independently include one or more of amino acids, peptides, or polypeptides;
R7-R22 each independently include one or more of hydrogen, amino acids, peptides, or polypeptides; and
n1-n6 each independently are about 0-20 and n7 is 0 (zero) or a positive integer.

2. The epoxide of claim 1, wherein the bisphenol-A substitute epoxide has a structure of Epoxide Formula 1C, Epoxide Formula 2C, Epoxide Formula 3C, Epoxide Formula 4C, or stereoisomer thereof.

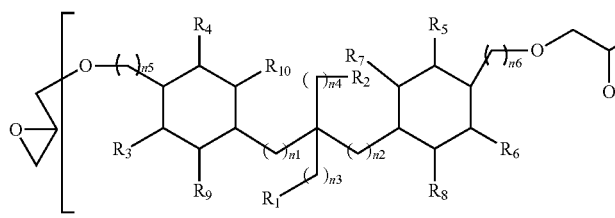
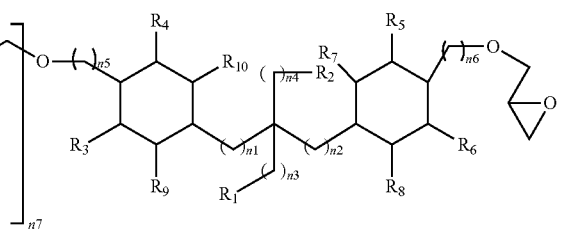

Epoxide Formula 1C

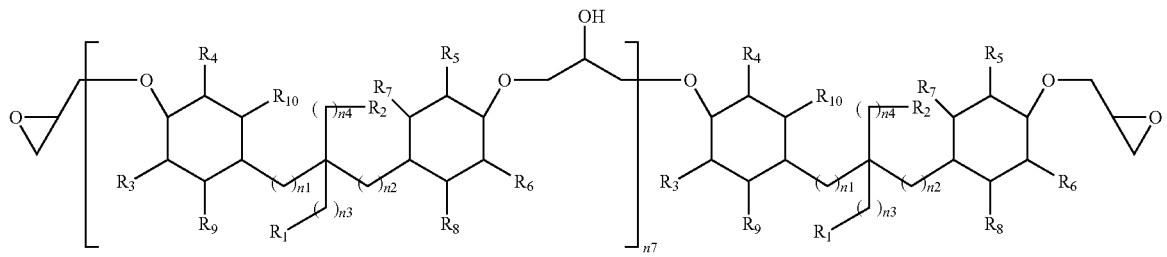

Epoxide Formula 2C

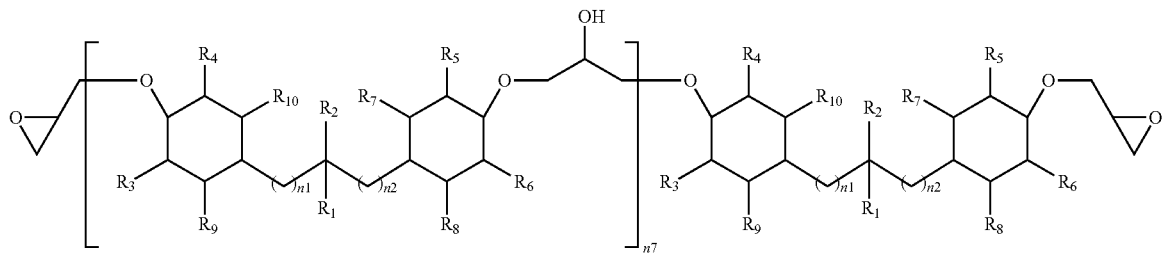

Epoxide Formula 3C

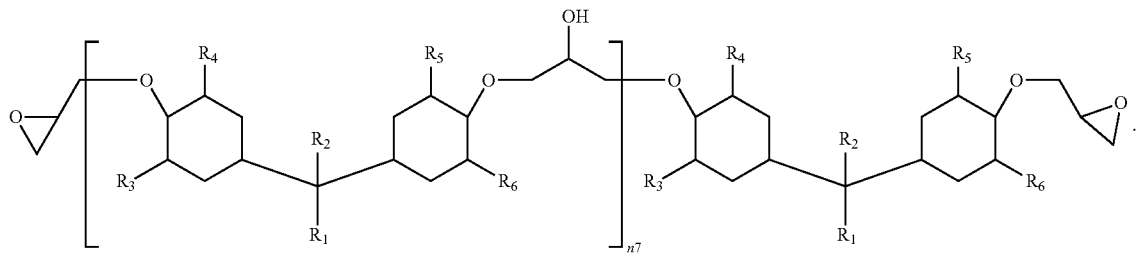

Epoxide Formula 4C

3. The epoxide of claim 1, wherein:
R1-R2 each independently include one or more of amino acids, peptides, or polypeptides;
R3-R6 each independently include one or more of amino acids, peptides, or polypeptides;
R7-R22 each independently include one or more of hydrogen, amino acids, peptides, or polypeptides; and
n1-n6 each independently are about 1-10 and n7 is a positive integer.

4. The epoxide of claim 1, wherein:
R1-R2 each independently include one or more of peptides or polypeptides;
R3-R6 each independently include one or more of peptides or polypeptides;
R7-R22 each independently include one or more of hydrogen, peptides or polypeptides; and
n1-n6 each independently are about 1-10 and n7 is a positive integer.

5. The epoxide of claim 1, wherein:
R1-R2 each independently include amino acids;
R3-R6 each independently include amino acids;
R7-R22 each independently include one or more of hydrogen or amino acids; and
n1-n6 each independently are about 1-10 and n7 is a positive integer.

6. The epoxide of claim 1, wherein:
R1-R2 each independently include polypeptides;
R3-R6 each independently include polypeptides;
R7-R22 each independently include one or more of hydrogen or polypeptides; and
n1-n6 each independently are about 1-10 and n7 is a positive integer.

7. The epoxide of claim 1, wherein:
R1-R2 each independently include one or more of polypeptides;
R3-R6 each independently include polypeptides;
R7-R22 each independently include polypeptides; and
n1-n6 each independently are and n7 is 0.

8. The epoxide of claim 1, wherein:
R1-R2 each independently include polypeptides;
R3-R6 each independently include one or more of amino acids, peptides, or polypeptides;
R7-R22 each independently include one or more of hydrogen, amino acids, peptides, or polypeptides; and
n1-n6 each independently are about 1-10 and n7 is a positive integer.

9. The epoxide of claim 2, wherein:
R1-R2 each independently include polypeptides;
R3-R6 each independently include polypeptides;
R7-R10 each independently include one or more of hydrogen or polypeptides; and
n1-n6 each independently are about 1-10 and n7 is 0.

10. The epoxide of claim 2, wherein:
R1-R2 each independently include peptides;
R3-R6 each independently include peptides;
R7-R10 each independently include one or more of hydrogen, or peptides; and
n1-n6 each independently are about 1-10 and n7 is a positive integer.

11. The epoxide of claim 2, wherein:
R1-R2 each independently include polypeptides;
R3-R6 each independently include polypeptides;
R7-R10 each independently include one or more of hydrogen or polypeptides; and
n1-n6 each independently are about 1-10 and n7 is a positive integer.

12. The epoxide of claim 2, wherein:
R1-R2 each independently include polypeptides;
R3-R6 each independently include polypeptides;
R7-R10 each independently include polypeptides; and
n1-n6 each independently are and n7 is 0.

13. The epoxide of claim 2, wherein:
R1-R2 each independently include one or more of amino acids, peptides, or polypeptides;
R3-R6 each independently include one or more of amino acids, peptides, or polypeptides;
R7-R22 each independently include one or more of hydrogen, amino acids, peptides, or polypeptides; and
n1-n6 each independently are and n7 is a positive integer.

* * * * *

UNITED STATES PATENT AND TRADEMARK OFFICE
CERTIFICATE OF CORRECTION

PATENT NO. : 9,018,335 B2
APPLICATION NO. : 13/139709
DATED : April 28, 2015
INVENTOR(S) : Ueda Page 1 of 3

It is certified that error appears in the above-identified patent and that said Letters Patent is hereby corrected as shown below:

In the specification

In Column 1, Line 8, delete "35 U.S.C. §371" and insert -- 35 U.S.C. § 371 --, therefor.

In Column 5, Line 15, in Formula 1C, delete " 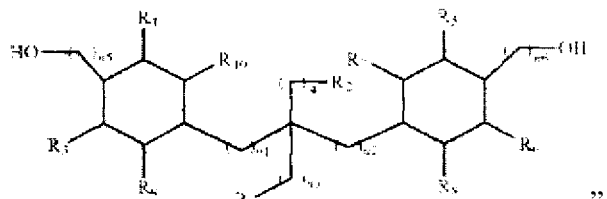 "
and insert -- 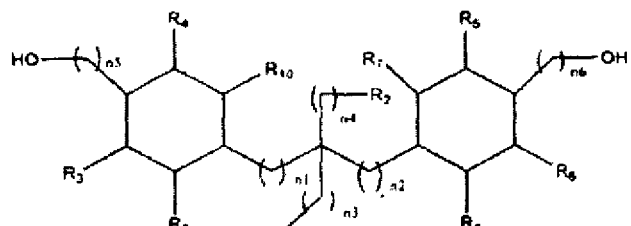 --, therefor.

In Column 5, Line 25, in Formula 2C, delete " 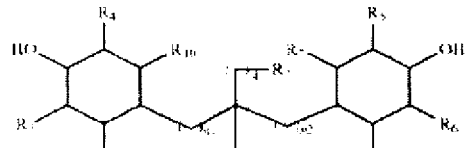 " and
insert -- 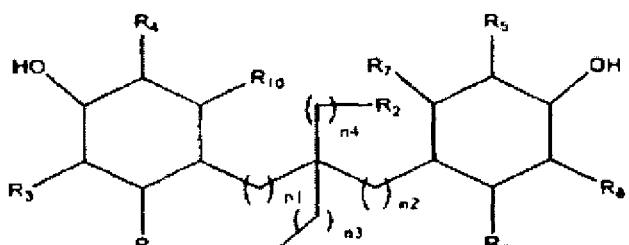 --, therefor.

Signed and Sealed this
Second Day of February, 2016

Michelle K. Lee
*Director of the United States Patent and Trademark Office*

CERTIFICATE OF CORRECTION (continued)
U.S. Pat. No. 9,018,335 B2

In the specification

In Column 5, Line 60, in Formula 1D, delete " 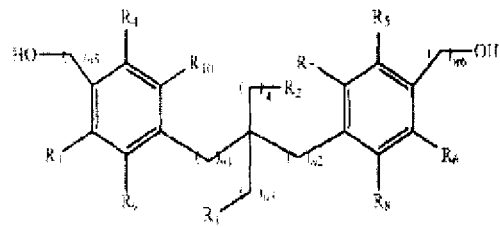 " and insert -- 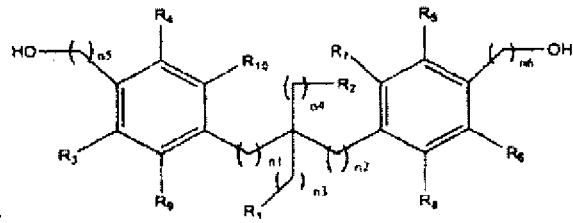 --, therefor.

In Column 6, Line 5, in Formula 2D, delete " 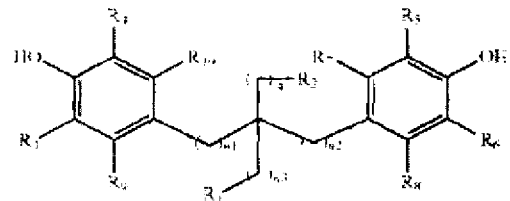 " and insert -- 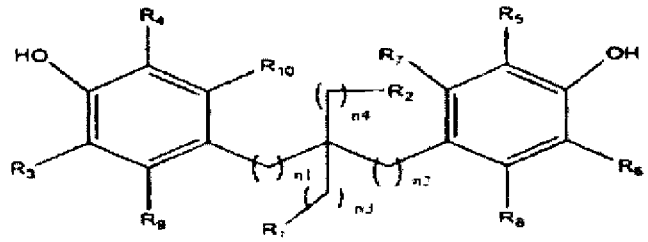 --, therefor.

In Columns 19-20, in Epoxide Formula 4B, delete

" 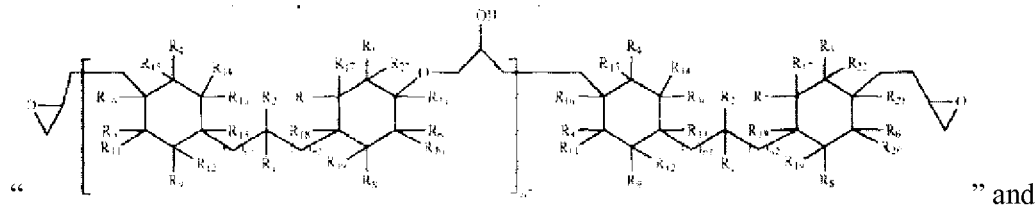 " and insert -- 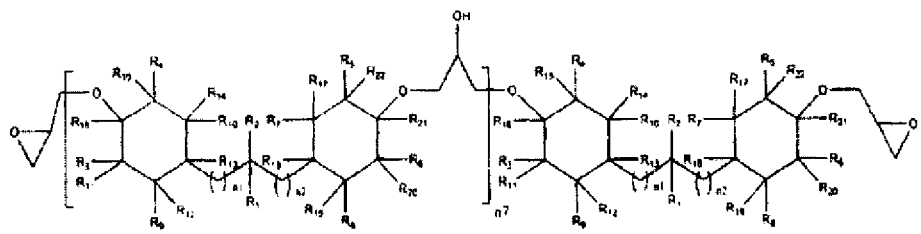 --, therefor.

CERTIFICATE OF CORRECTION (continued)
U.S. Pat. No. 9,018,335 B2

In the specification

In Column 32, Line 40, in Polycarbonate Formula 4C, delete

" 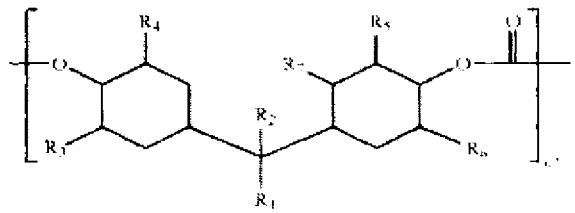 " and insert -- 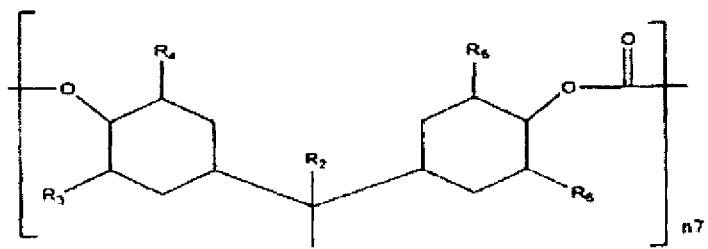 --, therefor.

In the claims

In Column 45, Line 55, in Claim 1, in Epoxide Formula 1B, delete

" 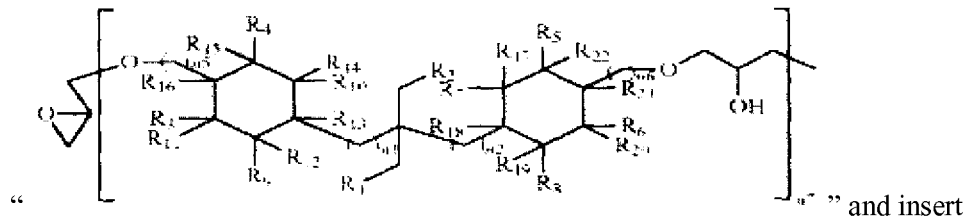 " and insert

-- 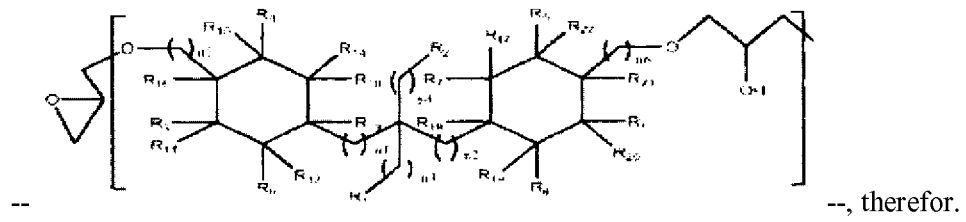 --, therefor.

In Column 48, Line 63, in Claim 7, delete "one or more of".